United States Patent
Willner et al.

(10) Patent No.: US 9,833,388 B2
(45) Date of Patent: Dec. 5, 2017

(54) CURABLE DENTAL MATERIAL

(71) Applicant: VOCO GmbH, Cuxhaven (DE)

(72) Inventors: Alexander Willner, Cuxhaven (DE); Manfred Thomas Plaumann, Cuxhaven (DE)

(73) Assignee: VOCO GMBH, Cuxhaven (DE)

(*) Notice: Subject to any disclaimer, the term of this patent is extended or adjusted under 35 U.S.C. 154(b) by 15 days.

(21) Appl. No.: 14/921,415

(22) Filed: Oct. 23, 2015

(65) Prior Publication Data

US 2016/0113846 A1   Apr. 28, 2016

(30) Foreign Application Priority Data

Oct. 23, 2014 (DE) .................. 10 2014 221 603

(51) Int. Cl.
*A61K 6/08* (2006.01)
*A61K 6/083* (2006.01)
*A61K 6/00* (2006.01)

(52) U.S. Cl.
CPC .......... *A61K 6/0835* (2013.01); *A61K 6/0005* (2013.01); *A61K 6/0008* (2013.01); *A61K 6/0073* (2013.01)

(58) Field of Classification Search
CPC .................. A61K 6/0005; A61K 6/0008
See application file for complete search history.

(56) References Cited

U.S. PATENT DOCUMENTS

| | | |
|---|---|---|
| 3,347,954 A | 10/1967 | Bredereck et al. |
| 3,715,331 A | 2/1973 | Molnar |
| 3,801,344 A | 4/1974 | Dietz |
| 3,808,170 A | 4/1974 | Rogers |
| 3,971,754 A | 7/1976 | Jurecic |
| 3,973,972 A | 8/1976 | Muller |
| 4,002,669 A | 1/1977 | Gross et al. |
| 4,302,376 A | 11/1981 | Walkowiak et al. |
| 4,323,348 A | 4/1982 | Schmitz-Josten |
| 4,443,587 A | 4/1984 | Schmitt et al. |
| 4,629,746 A * | 12/1986 | Michl .............. A61K 6/083 433/228.1 |
| 4,744,827 A | 5/1988 | Winkel et al. |
| 4,744,828 A | 5/1988 | Winkel et al. |
| 4,767,798 A | 8/1988 | Gasser et al. |

(Continued)

FOREIGN PATENT DOCUMENTS

| | | |
|---|---|---|
| CA | 2296227 | 7/2000 |
| CA | 2425953 | 10/2002 |

(Continued)

OTHER PUBLICATIONS

Riwotzki, K., et al., "Liquid-Phase Synthesis fo Doped Nanoparticles: Colloids of Luminescing LaPO4:Eu and CePO4:Tb Particles with a Narrow Particle Size Distribution," J. Phys. Chem., 2000, vol. 104, pp. 2824-2828.

(Continued)

*Primary Examiner* — Michael Pepitone
(74) *Attorney, Agent, or Firm* — Duane Morris LLP; Gregory M. Lefkowitz; Jason M. Nolan

(57) ABSTRACT

The present invention relates to a curable dental material, to a cured dental material producible therefrom by polymerization, to a method for producing the curable or cured dental material and to the use of the curable or cured dental material.

20 Claims, 1 Drawing Sheet

(56) References Cited

U.S. PATENT DOCUMENTS

| | | |
|---|---|---|
| 4,952,614 A | 8/1990 | Reiners et al. |
| 5,063,257 A | 11/1991 | Akahane et al. |
| 5,319,059 A | 6/1994 | Neuenschwander et al. |
| 5,780,668 A | 7/1998 | Rheinberger et al. |
| 5,847,025 A | 12/1998 | Moszner et al. |
| 5,936,006 A | 8/1999 | Rheinberger et al. |
| 6,124,491 A | 9/2000 | Wolter et al. |
| 6,191,191 B1 | 2/2001 | Harada et al. |
| 6,355,704 B1 | 3/2002 | Nakatsuka et al. |
| 6,362,251 B1 | 3/2002 | Alkemper et al. |
| 6,365,771 B1 | 4/2002 | Suzuki et al. |
| 6,613,812 B2 | 9/2003 | Bui et al. |
| 6,953,535 B2 | 10/2005 | Hecht et al. |
| 7,488,762 B2 | 2/2009 | Takano et al. |
| 7,601,767 B2 | 10/2009 | Ruppert et al. |
| 7,604,480 B2 | 10/2009 | Grundler et al. |
| 8,039,101 B2 | 10/2011 | Reynaud et al. |
| 8,129,444 B2 | 3/2012 | Hecht et al. |
| 8,183,305 B2 | 5/2012 | Neffgen et al. |
| 8,476,338 B2 | 7/2013 | Okubayashi et al. |
| 8,915,736 B2 | 12/2014 | Blömker et al. |
| 2007/0142495 A1 | 6/2007 | Neffgen et al. |
| 2008/0167399 A1 | 7/2008 | Utterodt et al. |
| 2008/0319104 A1* | 12/2008 | Klapdohr ............ A61K 6/0005 523/117 |
| 2009/0176194 A1* | 7/2009 | Qian ................ A61K 6/0023 433/228.1 |
| 2010/0087565 A1 | 4/2010 | Utterodt et al. |
| 2012/0082954 A1 | 4/2012 | Bloemker et al. |
| 2012/0115106 A1* | 5/2012 | Qian ................ A61K 6/0023 433/203.1 |
| 2015/0320646 A1 | 11/2015 | Kameya et al. |

FOREIGN PATENT DOCUMENTS

| | | |
|---|---|---|
| DE | 2419887 | 11/1974 |
| EP | 1563821 | 11/2006 |
| EP | 1839640 | 10/2007 |
| WO | 82/01006 | 4/1982 |
| WO | 2005/011621 | 2/2005 |

OTHER PUBLICATIONS

Huck-Jones, D., et al., "Chemische Identitat einzelner Partikel," Nachrighten aus der Chemie, Sep. 2014, vol. 62, pp. 886-887; with English abstract.

Database WPI, Week 201439, Thomson Scientific, London, GB; AN 2014-K87600 XP002455276.

Schulze, et al., "Artefacts in CBCT: a review," Dentomaxillofac. Radiol., 2011, vol. 40, No. 5, pp. 265-273.

* cited by examiner

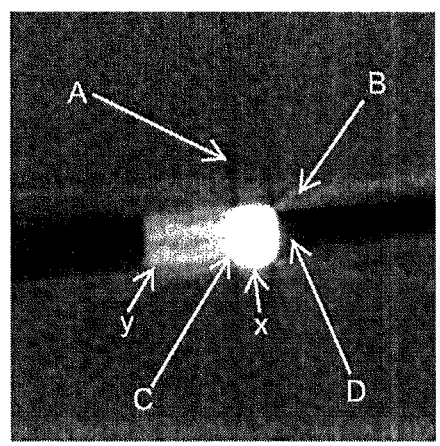

US 9,833,388 B2

CURABLE DENTAL MATERIAL

CROSS-REFERENCE TO RELATED APPLICATION

This application claims priority under 35 U.S.C. §119 to German Patent Application No. 102014221603.6 filed on Oct. 23, 2014 in European Patent Office, the disclosure of which is incorporated herein by reference in its entirety.

BRIEF SUMMARY OF THE INVENTION

The present invention relates to a curable dental material, to a cured dental material producible therefrom by polymerization, to a method for producing the curable or cured dental material and to the use of the curable or cured dental material. The curable or cured dental material may especially be used as tooth filling material, dental cement, dental lining material, free-flowing composite material (flow material), crown and bridge material, and for production of inlays, onlays and core build-up materials.

BRIEF DESCRIPTION OF THE DRAWINGS

FIG. 1 shows an example of artefacts in a two-dimensional cross section of an example test specimen.

DETAILED DESCRIPTION OF THE INVENTION

In dental practice, it is often of crucial significance to be able to clearly distinguish unnatural (i.e. synthetic) dental material in a previously treated tooth from the remaining natural tooth material. Such a distinction is possible, for example, by means of an x-ray image. Using an x-ray image, it is possible, in filling therapy, for example, to recognize marginal gaps. More particularly, the dentist is put in a position to identify even small marginal gaps between a filling composite (as an example of an unnatural, i.e. synthetic dental material) and the surrounding natural tooth material and, if necessary, to excavate very accurately. For this purpose, however, it is necessary that the filling composite (and quite generally synthetic dental materials) have sufficiently high x-ray opacity (also referred to as x-ray visibility) to be able to sufficiently strongly absorb x-rays during the x-ray imaging. This absorption ensures the necessary contrast in an x-ray image, in order to be able to distinguish between natural tooth material on the one hand and filling composite (or synthetic dental material) on the other hand. The filling composite (or quite generally tooth constituents composed of synthetic dental material) is regularly recognizable in an x-ray image from a lower degree of blackening. Sufficient x-ray opacity of a synthetic dental material thus very frequently allows reliable distinction between synthetic dental material and natural tooth material.

The natural x-ray opacity of a human tooth is typically 2 mm aluminium (Al) or less (dentine about 1.5 mm Al, enamel about 2 mm Al). Therefore, an x-ray-opaque synthetic dental material should generally have at least a value of greater than 2.5 mm Al. For example, a value of 10 mm Al means that a specimen of x-ray-opaque synthetic cured dental material of thickness 1 mm leads to blackening on an x-ray film identical to the blackening which is caused by a specimen of aluminium having a thickness of 10 mm (see further down in the text for the more exact determination of x-ray opacity). Particularly preferred x-ray opacities are within a range between 3.0 and 5.0 mm Al. The higher the x-ray opacity of a synthetic dental material (e.g. a filling composite), the better the distinguishability thereof from the natural tooth material in an x-ray image. A known synthetic dental material which is suitable, but also controversial, is amalgam, the x-ray opacity of which may be more than 10 mm aluminium (Al).

In the field of x-ray diagnostics, considerable advances have been achieved in the last few years, which allow ever more exact distinction between synthetic dental material and natural tooth material. In the last few years, a particular method which has become established in dental practices is known as digital volume tomography (DVT). A DVT system consists essentially of an x-ray source facing a detector (e.g. flat panel detector). In DVT, an object for analysis is penetrated by a conical or pyramidal, usually pulsed x-radiation (x-ray flash). Therefore, in the English-speaking world, the term CBCT (cone beam computer tomography) has become established. On the opposite side from the x-ray source, the signals attenuated by the object for analysis are detected as a two-dimensional projection on the detector. During the analysis, the unit composed of x-ray source and detector (gantry) rotates around the object for analysis, in order to create a multitude of individual images. In each individual image, attenuated greyscale x-ray images are obtained as a 2D projection. These individual images are used, by means of reverse projection, to calculate a three-dimensional reconstruction (greyscale coordinate picture, volume graphic) which images the anatomical structures of the object for analysis in the form of voxels of different grey levels. The three-dimensional reconstruction can be viewed either in the form of individual two-dimensional cross sections (tomograms) or in a 3D view.

DVT-generated images have been found to be particularly advantageous in dental implantology. They allow particularly careful planning of implants and the insertion thereof, taking account of the bone available. In the localization of wisdom teeth in preparation for surgical procedures, DVT-generated images have also been found to be very reliable.

Similarly to conventional x-ray diagnostics, x-ray opacity plays a crucial role in the distinction between synthetic dental material and natural tooth material in DVT as well. There is thus a constant need to advantageously adjust the x-ray opacity of curable dental materials which are processed further by means of polymerization of polymerizable monomers to give cured synthetic dental materials.

Essentially two methods are available for this purpose:

Method I: The use of polymerizable monomers in curable dental materials, wherein the monomers are bonded by means of covalent bonds to x-ray-absorbing atoms/compounds.

Method II: The use of curable dental materials comprising x-ray-opaque inorganic fillers (e.g. oxides and/or carbonates of selected metals).

According to method I, in a curable dental material, monomers, particularly polymerizable monomers, bonded covalently to halogen atoms (e.g. bromine atoms), for example, are used, such that the desired x-ray opacity is achieved in a corresponding synthetic dental material. Examples of this are disclosed in the international patent application with the publication number WO 82/01006 A1. WO 82/01006 A1 relates to homo- or copolymers of (meth) acrylate esters comprising covalently bonded x-ray-absorbing atoms ("homo- or copolymer of a (meth)acrylate ester into which atoms capable of absorbing x-radiation are incorporated by covalent bonding", WO 82/01006 A1, claim 1), where these atoms include halogen atoms ("the atoms comprise halogen atoms capable of absorbing x-radiation", WO 82/01006 A1, claim 2) and the halogen atoms include bromine atoms ("the halogen atoms capable of absorbing x-radiation comprise bromine atoms"), WO 82/01006 A1, claim 3).

The German patent application having the publication number DE 21 21 480 A1, entitled "Monomer-soluble x-ray-opaque methacrylate particles", "is concerned with fine particulate methacrylate particles in bead form, wherein aliphatic halides are distributed through the beads, in order to result in an x-ray-opaque material". DE 21 21 480 A1 goes on to say that "The aliphatic halide compounds contain either bromine or iodine. In order to obtain the favourable particulate methacrylate polymer, it is necessary that the specific halide component comprises at least 50% by weight of the aliphatic halide molecule." (DE 21 21 480 A1, page 8, first complete paragraph).

Subject-matter of the publication DE 35 02 594 A1 is a "X-ray opaque dental material" (title of corresponding EP-document EP 01 89 540 A2).

Subject-matter of the publication DE 19617 931 A1 is a "Polymerisable dental material containing a filler" (title of corresponding EP-document EP 08 03 240 A2).

DE 10 2004 017 124 A1 relates to "Hardening dental materials featuring adjustable translucence" (title of corresponding WO-document WO 2005 097 043 A1).

EP 2 436 363 A2 relates to a "Compound comprising a monomer with a polyalicyclic structure element for filling and/or sealing a root canal" (title). The composition is a curable dental composition consisting of or comprising "(a) a monomer component [ . . . ], (b) one or a plurality of initiators and/or catalysts, and (c) a filler component".

The German patent application having the publication number DE 41 11 914 A1 relates to "a material composed of plastic together with x-ray-absorbing comonomer". According to claim 1 in DE 41 11 914 A1, the "material [is] composed of plastic with covalently bonded x-ray contrast agents".

The European patent application having the publication number EP 0 685 454 A1 relates to "x-ray-opaque esters and amides of iodine-substituted benzoic acid [ . . . ] and to polymers and dental materials produced therefrom (EP 0 685 454 A1, page 2 lines 1 and 2). The dental materials disclosed in EP 0 685 454 A1 are suitable as "filling composites, luting cements, adhesion promoters (bondings) and for production of artificial teeth, inlays, implants, crowns, bridges and dentures, preferably as tooth filling material, luting cement or bonding" (EP 0 685 454 A1, page 4 lines 26 to 29).

However, curable dental materials which are produced by method I regularly also have disadvantages.

As well as quite complex synthesis methods for preparation of the corresponding polymerizable monomers with covalently bonded x-ray-absorbing atoms/compounds, high proportions of x-ray-absorbing atoms/compounds are generally needed in the polymerizable monomers in order to achieve sufficient x-ray opacity. However, this often leads to difficulties in the free-radical polymerization of the polymerizable monomers, since the chemical incorporation of elements having high atomic weights (e.g. iodine, bromine, etc.) frequently leads to chain terminations in the formation of the polymers (i.e. of the cured dental materials). The result of this is that polymerizable monomers of this kind frequently have a very low propensity to polymerize, and cured dental materials produced therefrom frequently have a low degree of polymerization. This regularly leads to poor mechanical properties in the cured dental material.

As already shown above, the x-ray-absorbing atoms/compounds used include organic halogen compounds which frequently comprise the elements iodine and/or bromine. However, these compounds are often of low stability and of low compatibility with the further constituents of a curable dental material and have a tendency to discolour the cured dental material. Another observation which has been made in in-house experiments is that such compounds have a tendency to migrate out of the polymeric matrix of a cured dental material, which frequently leads to weakening of the mechanical network.

According to method II, x-ray-opaque inorganic fillers (for example oxides and/or carbonates of lanthanum, strontium, hafnium or tantalum, and halogen salts of ytterbium) are used.

The German patent application having the publication number DE 24 58 380 A1, entitled "Tooth filling compound", "relates to tooth filling compounds for dental repair practice, such as fillings, lutes, inlays and the like". On page 3, second complete paragraph, DE 24 58 380 A1 says "The filling compounds according to the invention contain non-toxic atoms which absorb x-rays, primarily lanthanum, strontium and tantalum, and secondarily hafnium, in the form of oxides or carbonates."

The German patent application having the publication number DE 23 47 591 A1, entitled "Glass ceramic as filler for polymerizing dental filling compounds" discloses a "[c]olourless transparent glass ceramic [ . . . ] having high absorption for x-rays, for use in mixed plastic-glass ceramic bodies for dental filling compounds [ . . . ]" (DE 23 47 591 A1, claim 1). The following glass ceramic materials are disclosed: $SiO_2$, $Al_2O_3$, $Li_2O$, $P_2O_5$, MgO, ZnO, $ZrO_2$, $Ta_2O_5$, $La_2O_3$.

The US patent applications having publication numbers U.S. Pat. No. 3,801,344 A and U.S. Pat. No. 3,808,170 A relate to a tooth filling material comprising a mixture of finely distributed inorganic materials and x-ray-opaque glass fillers (respectively, "tooth filling and facing composition having a mixture of finely divided inorganic material and a radiopaque glass as a filler and an organic polymer as a binder" and an "epoxy resin derived from bisphenol A and a methacrylic acid compound crosslinked with a diester or triester of methacrylic acid as the matrix, and a barium-containing glass filler". Both documents disclose the use of barium oxide for achievement of x-ray-opaque properties.

The European patent application having the publication number EP 0 011 735 A2, entitled "X-ray-opaque dental materials based on organic polymers in paste form" relates to "x-ray-opaque dental materials based on organic polymers in paste form consisting [ . . . ] of a) polymerizable binders, b) crosslinked polymers, c) x-ray contrast agents and optionally d) finely divided, non-x-ray-opaque inorganic fillers" (EP 0 011 735 A2, claim 1). With regard to the x-ray contrast agents, the following is stated at page 8 lines 18 to 25: "Barium compounds are of particularly good suitability, for example barium sulphate, barium fluoride and barium silicate. Also suitable are compounds of bismuth, for example bismuth oxynitrate, zirconium, for example zirconium dioxide, and lanthanum, for example lanthanum oxide, and compounds of thorium and the rare earth metals. In addition, it is possible to use inorganic and organic iodine compounds as x-ray contrast agents."

The European patent application having the publication number EP 0 189 540 A2, entitled "X-ray-opaque dental material" relates to "x-ray-opaque dental materials such as, for example, filling materials, dental cements, crown and bridge materials, prosthesis materials, and the use thereof for production of artificial teeth, inlays, implants and dentures" (EP 0 189 540 A2, page 1 lines 1 to 5). The x-ray-opaque dental material disclosed in EP 0 189 540 A2 is characterized in that "it comprises a fluoride of the rare earth metals (elements 57 to 71) [also referred to as RE fluorides] of the Periodic Table of the Elements or a mixture of these fluorides" (EP 0 189 540 A2, claim 1). Particular preference is given to ytterbium trifluoride (EP 0 189 540 A2, claim 3). The following is stated at page 3 lines 30 to 36: "The mean particle size of the primary particles may vary. In the case of a micro-filled tooth filling material, it is in the range from 5 to 700, especially 20 to 500, preferably 50 to 300 nm. The mean primary particle size may optionally also be in the range from 700 nm to 5 μm." The following is also stated: "The content of RE fluorides, based on the total weight, is between 1% and 50%, especially 5% to 40%, preferably between 10% and 25%" (EP 0 189 540 A2, page 4 lines 1 to 3).

The European patent application having the publication number EP 2 548 546 A1, entitled "X-ray-opaque infiltrant" relates to an "infiltrant for dental application, comprising crosslinking monomers, and the use thereof for prevention or treatment (sealing) of carious enamel lesions" (paragraph [0001] in EP 2 548 546 A1). Claim 1 of EP 2 548 546 A1 discloses an "infiltrant for dental application, comprising crosslinking monomers and initiator and having a dynamic viscosity, measured at 23° C., of 50 mPas or less, characterized in that the infiltrant includes at least one nanoscale x-ray-opaque filler and/or an x-ray-opaque organic compound". Paragraph [0024] discloses the following: "Among the salts of the rare earth metals (elements 57-71), scandium or yttrium, the trifluorides are preferred. The preferred rare earth elements include lanthanum, cerium, samarium, gadolinium, dysprosium, erbium or ytterbium. Among the salts thereof, the fluorides are preferred, especially ytterbium fluoride ($YbF_3$). Preferred barium and strontium salts are fluorides, phosphates and sulphates, especially the sulphates."

According to paragraph [0028] in EP 2 548 546 A1, the nanoscale x-ray opaque fillers "preferably have the following median primary particle sizes $d_{50}$ or ranges for these particle sizes:
 smaller than 1000 nm, smaller than 700 nm, smaller than 500 nm, smaller than 200 nm, smaller than 100 nm, smaller than 25 nm,
 between 1 nm and 80 nm, between 4 nm and 60 nm, between 6 nm and 50 nm, between 0.5 nm and 22 nm, between 1 nm and 20 nm, between 1 nm and 10 nm or between 1 nm and 5 nm."

In paragraph [0029], EP 2 548 546 A1 says: "Particular preference is given to nonaggregated and nonagglomerated nanoscale fillers present in individualized form. Preference is further given to fillers having unimodal particle size distribution."

According to claim 8 of EP 2 548 546 A1, "the content of the nanoscale x-ray-opaque filler in the infiltrant, based on the total mass of the infiltrant with all its constituents, is 1% by weight to 30% by weight, preferably 5% by weight to 25% by weight, further preferably 10% by weight to 20% by weight or 1% by weight to 5% by weight, 5% by weight to 10% by weight, 10% by weight to 15% by weight or 15% by weight to 20% by weight [ . . . ]".

The international patent application having the publication number WO 2005/011621 A1, entitled "X-ray-opaque dental material comprising surface-modified nanoparticles", "relates to an x-ray-opaque dental material [ . . . ] comprising surface-modified salts of the rare earth metals, of scandium, yttrium, barium or strontium, or a tungstate, and the use thereof in dental technology" (WO 2005/011621 A1, page 1, first complete paragraph). According to claim 1 of WO 2005/011621 A1, the dental material comprises "at least one filler [ . . . ] which is selected from salts of barium, strontium, the rare earth metals, scandium or yttrium, or from tungstates, [wherein] [ . . . ] the filler is in the form of surface-modified nanoparticles having a mean particle size of less than 25 nm, the surface of which has been modified with an organic compound which binds to the nanoparticles by an N-, P-, S- and/or O-containing functional group". On page 4, penultimate complete paragraph, WO 2005/011621 A1 says: "The preferred rare earth metals include lanthanum, cerium, samarium, gadolinium, dysprosium, erbium or ytterbium. Among the salts thereof, the fluorides are preferred, especially ytterbium trifluoride ($YbF_3$)."

According to page 10 in WO 2005/011621 A1, last paragraph, the surface-modifying compounds are preferably "an organophosphorus compound or a mono- or disubstituted amine". In the penultimate paragraph on page 10, it is disclosed that this surface-modifying organic compound does "not just [have] a positive [effect] on the later dispersion in a dental material. In addition, it has a limiting effect on the crystal growth and leads to the above-specified small particle sizes of less than 25 nm in a narrow particle size distribution."

The German patent application having the publication number DE 36 09 038 A1, entitled "X-ray-opaque polymerizable dental compositions", "relates to novel x-ray-opaque polymerizable dental compositions, especially tooth filling compounds" (DE 36 09 038 A1 page 2 line 35). According to claim 1 in DE 36 09 038 A1, these contain "a sparingly soluble heavy-metal fluoride from the group of $YF_3$ and complex heavy metal fluorides of the general formula $M^{II}M^{IV}F_6$ [ . . . ] where $M^{II}$ is a calcium, strontium or barium ion and $M^{IV}$" is a titanium, zirconium or hafnium ion". According to claim 5 in DE 36 09 038 A1, a particularly preferred sparingly soluble heavy-metal fluoride is $YF_3$.

The German patent application having the publication number DE 198 46 556 A1 "is directed to a dental material and a method for production thereof. The invention likewise relates to porous glass ceramics, to a process for production thereof and use" (DE 198 46 556 A1, page 2 lines 3 and 4). Claim 1 in DE 198 46 556 A1 says: "Dental material based on [ . . . ] an inorganic filler (A) [ . . . ] characterized in that the inorganic filler (A) is a porous glass ceramic having micro- and/or mesopores laden with polymerizable, ethylenically unsaturated monomers, epoxides, ormocers, liquid-crystalline monomers, oxetanes, spiro-orthoesters or -carbonates, or with the polymerized form thereof". According to claim 5 of DE 198 46 556 A1, "the filler (A) comprises oxides of the metals of main groups 1 to 4 and oxides of the metals of the transition groups [ . . . ]". Oxides for use with preference are $TiO_2$, $ZrO_2$, BaO and $WO_3$, particular preference being given to $ZrO_2$ (DE 198 46 556 A1, page 5 lines 32 and 33).

The US patent having the publication number U.S. Pat. No. 8,476,338 B2 relates to a dental composite ("a dental composite resin, that can be used as a substitute for a part of a natural tooth or an entire natural tooth in the field of dental treatment" (U.S. Pat. No. 8,476,338 B2, column 1 lines 10 to 14). According to claim 7 of U.S. Pat. No. 8,476,338 B2, the composite comprises, as well as "a polymerizable monomer (A), inorganic particles (B), inorganic particles (C) and inorganic ultrafine particles (D)".

Curable dental materials produced according to method II regularly also have disadvantages.

In general, increasing x-ray opacity is observed with an increasing proportion of x-ray-opaque, particulate inorganic fillers. However, satisfactory x-ray opacity is not achieved until the proportion of x-ray-opaque inorganic fillers is comparatively high. However, a comparatively high proportion of such particulate fillers frequently leads to increased visual opacity (i.e. to comparatively low translucence) in cured dental materials. The effect of this comparatively low translucence is that the cured dental material is no longer optimally matched in aesthetic terms to the appearance of the surrounding natural tooth material. Moreover, insufficient translucence in the case of light-initiated polymerization frequently leads to limited (inadequate) curing depth/penetration depth of the light. The light required for the polymerization does not penetrate sufficiently deep into the curable dental material, and so the material polymerizes only incompletely. This can lead in turn to faulty restorations. In well-adjusted dental materials, the proportion of x-ray-opaque inorganic fillers in a cured dental material having an x-ray opacity considered to be acceptable frequently leads to a reduction in translucence which is still acceptable. The translucence of the cured dental material crucially depends additionally on the refractive indices of the organic and inorganic constituents. It is generally the case that the closer these refractive indices are to one another, the more translucent the cured dental material is. An optimal mixture would thus be one in which the inorganic substances and the organic substances have identical refractive indices. Typically, however, the refractive indices of the organic constituents (for example the polymerized monomers) are in the range from 1.45 to 1.55, whereas the refractive indices of the inorganic constituents (for example the x-ray-absorbing inorganic fillers) are within a range greater than 1.55. The result of this is that complex adjustments have to be undertaken with regard to the refractive indices of the constituents to produce sufficiently translucent, x-ray-opaque dental materials.

In a multitude of x-ray-opaque dental materials (frequently in addition to the aforementioned x-ray-opaque inorganic particulate fillers), x-ray-opaque dental glasses (comprising heavy atoms) are processed, and these frequently make up the main proportion of the amount of filler. Elements of relatively high atomic number (heavy atoms) in the dental glasses bring about a higher x-ray opacity compared to dental glasses containing no elements of relatively high atomic number. The x-ray-opaque dental glasses generally enable sufficient translucence combined with acceptable x-ray opacity. However, what would be desirable here too would be an extremely high translucence combined with very good x-ray opacity. However, x-ray-opaque dental materials based on x-ray-opaque dental glasses likewise have some disadvantages.

Firstly, dental glasses are prone to hydrolysis, and so there is regularly a risk that ions will pass over from the dental glasses (in the cured dental material) into the oral cavity. As well as degradation of the cured dental material, this can also lead to human toxicological damage.

Secondly, it has been found in some cases that cured dental materials filled with dental glasses can have comparatively low abrasion resistance, compared, for example, to a cured dental material based on quartz. This is because of the comparatively low hardness of standard dental glasses compared to quartz.

Furthermore, it has been observed in individual cases that dental materials filled with dental glass can be polished to a shine only to an inadequate degree, if at all, as a result of the particle sizes of standard dental glasses. Thus, an observation made in these cases was that voluminous filler particles in particular break out of a filling during polishing. The effect of this is that small holes remain. In addition, the filler particles which have broken out exert an emery effect on the surrounding surface, and so it is barely possible to polish dental materials filled with dental glasses to a shine in these cases, and they have aesthetic defects. Cured dental materials polished to a shine are generally obtained especially when particulate fillers having a mean particle size of about 0.04 µm are used.

In the above-described DVT as well, particular cured dental materials show better results than others. As in any imaging method, image distortions and especially what are called artefacts occur in DVT. An image artefact is a structure visible in the image produced which is not reflected or does not have a corresponding structure in the object for analysis. The causes of the distortions and artefacts are various and relate both to the data recording of the primary data (artefacts are caused, for example, by detector noise, scattering of the x-rays, movement of the patient) and to the mathematical image reconstructions after data recording. Artefacts are observed in DVT images mainly in the form of stripes, linear structures and shadows, particularly frequently adjacent to synthetic dental materials or dental reconstructions. The synthetic dental materials or dental reconstructions in question generally consist of metal (titanium, gold, amalgam etc.) or contain compounds comprising elements of higher atomic number (e.g. barium, ytterbium, etc.), and so they have a certain x-ray opacity. It is specifically this x-ray opacity, i.e. the ability to attenuate x-rays, which is important for conventional x-ray diagnostics, that also promotes the formation of extinguishment and beam hardening artefacts in DVT (beam hardening artefacts arise through detection of short-wave high-energy x-ray radiation which is present in the x-ray spectrum alongside long-wave low-energy x-ray radiation and is absorbed only to a low degree at x-ray-opaque structures and thus reaches the detector unhindered, compared to the low-energy x-ray radiation). In practice, these artefacts are manifested in DVT images particularly in the form of what are called hyper- or hypodense regions, which can easily be misinterpreted as secondary caries (for exact explanations of the artefacts see: R. Schulze et al., "Artefacts in CBCT: a review", Dentomaxillofacial Radiology, 40, 265-273 (2011)). It is suspected that curable dental materials directed specifically to the requirements of DVT lead to comparatively fewer artefacts in a DVT image.

There is thus an urgent need to provide curable or cured dental materials which
  are producible in a simple manner,
  have high translucence,
  high x-ray opacity,
  an attractive appearance
  and good physical properties,
  and lead to DVT images having a comparatively low level of artefacts, especially when used in DVT.

It was therefore an object of the present invention to provide a curable dental material which, after polymerization of polymerizable monomers (i.e. in the cured state) and during a DVT measurement, leads to a comparatively low level of artefacts in the resulting DVT images (compared to curable dental materials that are otherwise customary, such as the above materials known from the prior art) and additionally has several or all of the following properties:
  producible in a simple manner,
  high translucence,
  high x-ray opacity, an attractive appearance, especially good polishability, good physical properties, for example (and preferably) good flexural strength and/or good abrasion resistance.

This object is achieved by a curable dental material producible by mixing starting materials, wherein the starting materials to be mixed are exclusively one, two, three or more than three polymerizable monomers which form the total amount (A) of the polymerizable monomers in the curable dental material, one, two, three or more than three particulate fillers which form the total amount (B) of the particulate fillers in the curable dental material, and one, two, three or more than three auxiliaries which form the total amount (C) of the auxiliaries in the curable dental material, wherein
the curable dental material comprises a component (B1) which forms part of the total amount (B), consisting of the total amount of the following that are present in the curable dental material:
(a) nonaggregated and nonagglomerated filler particles having a particle size in the range from 25 to 120 nm of ytterbium fluoride
and
(b) nonaggregated and nonagglomerated filler particles having a particle size in the range from 25 to 120 nm of barium sulphate,
wherein
the proportion of component (B1) is
2.5% by weight or greater than 2.5% by weight, based on the total mass of the curable dental material,
and
90% by weight or greater than 90% by weight, based on the total mass of filler particles of ytterbium fluoride and barium sulphate in the curable dental material.

It is not necessary for both species (a) and (b) to be present in a curable dental material of the invention. In practice, the use of just one species (a) or (b) is frequently advantageous; see the remarks and examples further down. If just one of the species (i.e. (a) or (b)) is present in the curable dental material of the invention, the total amount thus corresponds to the amount of these individual species (a) or (b) present in the curable dental material of the invention.

The figures given above and below in conjunction with the teaching of the invention for particle sizes include the range limits. For example, a particle size in the range from 25 nm to 120 nm means in the range from 25 nm to 120 nm inclusive.

In the discussion of the curable dental materials of the invention (as described above) or of cured dental materials of the invention produced therefrom by polymerization of polymerizable monomers, the expression "ytterbium fluoride", for terminology purposes, includes "ytterbium(III) fluoride" and "ytterbium trifluoride" (with regard to the cured dental materials of the invention, see further down in the text).

The
(a) nonaggregated and nonagglomerated filler particles having a particle size in the range from 25 to 120 nm of ytterbium fluoride
and the
(b) nonaggregated and nonagglomerated filler particles having a particle size in the range from 25 to 120 nm of barium sulphate
are typically crystalline; however, proportions of amorphous particles and proportions of particles having both crystalline and amorphous regions are not ruled out. Preferably (and typically), component (B1) thus comprises crystalline particles.

The
(a) nonaggregated and nonagglomerated filler particles having a particle size in the range from 25 to 120 nm of ytterbium fluoride
and the
(b) nonaggregated and nonagglomerated filler particles having a particle size in the range from 25 to 120 nm of barium sulphate
typically have a very substantially spherical (ball-like) shape. In determining the aforementioned particle size, the starting point used for the calculation is that all the particles have a spherical (ball-like) shape (for details of the determination and calculation see below under examples, points I.d to I.f).

Preferably, in respect of the total amount of the nonaggregated and nonagglomerated filler particles of ytterbium fluoride and the nonaggregated and nonagglomerated filler particles of barium sulphate in the total amount (B), the mean particle size of these filler particles is in the range from 25 to 120 nm.

More preferably, in respect of the total amount of the filler particles of ytterbium fluoride and the filler particles of barium sulphate in the total amount (B), the mean particle size is in the range from 25 to 120 nm.

Where a "mean particle size" is discussed above or below in configurations of the invention, this is the volume-based mean particle size.

Preference is thus given to a curable dental material of the invention (as described above, preferably as defined above as preferred), producible by mixing starting materials, wherein the starting materials to be mixed are exclusively:

one, two, three or more than three polymerizable monomers which form the total amount (A) of the polymerizable monomers in the curable dental material, one, two, three or more than three fillers which form the total amount (B) of the fillers in the curable dental material, and one, two, three or more than three auxiliaries which form the total amount (C) of the auxiliaries in the curable dental material, wherein
the curable dental material comprises a component (B1) which forms part of the total amount (B), consisting of the total amount of the following that are present in the curable dental material:
(a) nonaggregated and nonagglomerated filler particles having a particle size in the range from 25 to 120 nm of ytterbium fluoride
and
(b) nonaggregated and nonagglomerated filler particles having a particle size in the range from 25 to 120 nm of barium sulphate,
wherein
the proportion of component (B1) is
2.5% by weight or greater than 2.5% by weight, based on the total mass of the curable dental material,
and
90% by weight or greater than 90% by weight, based on the total mass of filler particles of ytterbium fluoride and barium sulphate in the curable dental material
and
the filler particles in the total amount of filler particles of ytterbium fluoride and filler particles of barium sulphate in the total amount (B) have a mean particle size in the range from 25 to 120 nm, the filler particles in the total amount of filler particles of ytterbium fluoride and the filler particles of barium sulphate in the total amount (B) preferably having a mean particle size in the range from 25 to 80 nm.

Particular (preferred) properties of the curable dental materials of the invention (for example the refractive indices of the filler particles in component (B1)) can be determined in the curable dental material of the invention itself only with quite a high level of complexity, which is why the emphasis in the above definition is on the starting materials used among other features. However, (preferably gentle) mixing of the abovementioned starting materials typically does not result in any change in the proportions and compositions of the total amounts (A), (B) and (C). There is likewise generally no conversion of matter triggered by the (gentle) mixing. The present invention therefore also relates to a curable dental material consisting of one, two, three or more than three polymerizable monomers which are the total amount (A) of the polymerizable monomers in the curable dental material, one, two, three or more than three fillers which are the total amount (B) of the fillers in the curable dental material, and one, two, three or more than three auxiliaries which are the total amount (C) of the auxiliaries in the curable dental material, wherein the curable dental material comprises a component (B1) which forms part of the total amount (B), consisting of the total amount of the following that are present in the curable dental material:

(a) nonaggregated and nonagglomerated filler particles having a particle size in the range from 25 to 120 nm of ytterbium fluoride and (b) nonaggregated and nonagglomerated filler particles having a particle size in the range from 25 to 120 nm of barium sulphate, wherein the proportion of component (B1) is 2.5% by weight or greater than 2.5% by weight, based on the total mass of the curable dental material, and 90% by weight or greater than 90% by weight, based on the total mass of filler particles of ytterbium fluoride and barium sulphate in the curable dental material.

The statements made above and below with regard to the curable dental material of the invention, producible by mixing particular starting materials, apply correspondingly to a curable dental material of the invention consisting of the aforementioned total amounts (A), (B) and (C).

In the curable dental material of the invention (as described above, preferably as defined above as preferred), producible by mixing starting materials, the fillers which form the total amount (B) of the fillers in the curable dental material comprise a component (B1). This component (B1) consists of the total amount of the following that are present in the curable dental material:

(a) nonaggregated and nonagglomerated filler particles having a particle size in the range from 25 to 120 nm of ytterbium fluoride and (b) nonaggregated and nonagglomerated filler particles having a particle size in the range from 25 to 120 nm of barium sulphate.

More preferably, 95% by weight or more, preferably 98% by weight or more, more preferably 99% by weight or more and especially preferably 100% by weight of the total amount of the filler particles of ytterbium fluoride and the filler particles of barium sulphate form the total amount of the filler particles of component (B1) that are present in the curable dental material. It is preferably the case that the proportion of component (B1) is 95% by weight or more, preferably 98% by weight or more, more preferably 99% by weight or more and especially preferably 100% by weight, based on the total mass of filler particles of ytterbium fluoride and barium sulphate in the curable dental material.

All filler particles that cannot be allotted to component (B1) are allotted to a further component (B2), for example filler particles that do not consist of ytterbium fluoride or barium sulphate or have a different particle size.

If the curable dental material comprises, for example, only filler particles of ytterbium fluoride and/or barium sulphate, but a fraction of these filler particles of ytterbium fluoride and/or barium sulphate, for example, is in aggregated and/or agglomerated form, this fraction is not allotted to component (B1) but to component (B2), in which case component (B2) (difference) is equal to the total amount (B) (minuend) minus component (B1) (subtrahend). Accordingly, the total amount (B) is the sum total of component (B1) (summand) and component (B2) (summand).

Preferably, 95% by weight or more, more preferably 98% by weight or more, especially preferably 99% by weight or more and most preferably 100% by weight of the filler particles consist of (i) ytterbium fluoride having a particle size in the range from 25 to 120 nm and (ii) of barium sulphate having a particle size in the range from 25 to 120 nm in nonaggregated and nonagglomerated form (i.e. primary particles), based on the total mass of filler particles of barium sulphate and of ytterbium fluoride in the curable dental material of the invention, all of which have a particle size in the range from 25 to 120 nm.

If the starting materials comprise, for example, filler particles of ytterbium fluoride and/or barium sulphate having, for example, a particle size of less than 25 nm or greater than 120 nm, these are likewise not allotted to component (B1) but to component (B2).

Preferably, 95% by weight or more, more preferably 98% by weight or more, especially preferably 99% by weight or more and most preferably 100% by weight of the nonaggregated and nonagglomerated filler particles of (i) ytterbium fluoride and (ii) barium sulphate have a particle size in the range from 25 to 120 nm, based on the total mass of the filler particles of barium sulphate and of ytterbium fluoride in the curable dental material of the invention, all of which are nonaggregated and nonagglomerated.

The proportion of component (B1) is 2.5% by weight or is greater than 2.5% by weight, based on the total mass of the curable dental material. In in-house studies, it has been found that a curable dental material of the invention (as described above, preferably as defined above as preferred) has good translucence, good x-ray opacity and good physical properties, especially with occurrence of comparatively few artefacts (or less pronounced artefacts) in DVT images. Curable dental materials producible by mixing the abovementioned starting materials, where the proportion of component (B1) is (much) less than 2.5% by weight, based on the total mass of the curable dental material, according to in-house studies, in many cases, do not show any significant reduction in artefacts in DVT images. Moreover, it has been observed in a multitude of cases that a curable dental material having a proportion of less than 2.5% by weight does not have satisfactory x-ray opacity, especially in the absence of sufficient amounts of other x-ray-opaque particulate fillers.

Especially the filler particles of component (B1) contribute to the comparatively small number of artefacts in DVT images that have been made of a cured dental material based on the curable dental material of the invention.

Filler particles of component (B1) have preferably been subjected to organic surface modification. For organic surface modification, compounds of the general X-Sp-Y type are suitable with preference, where "X" and "Y" are functional groups joined to one another by a linker (spacer, "Sp").

The functional "X" group is preferably selected such that it can enter into a corresponding bond to the surface of the filler particle with complex formation. Suitable examples are groups of the phosphate, phosphonate, carboxylate, dithiophosphate, dithiophosphonate, amine and amide type. The surface binding of the compound for an organic surface modification to the filler particles can be improved by multiple formation of a functional group (polyphosphates, polycarboxylates).

Suitable (and hence preferred) linkers (spacers, "Sp") are linear or branched alkyl chains, aromatics or combinations of these groups, each of which may be interrupted by heteroatoms such as O, N, S or P.

The functional "Y" group imparts compatibility of the filler particles with the total amount of the polymerizable monomers (A), for example by hydrophobization. Preference is given to linear or branched alkyl, arenyl or alkenyl groups, the latter offering the advantage of being incorporated in the polymerization of the polymerizable monomers, which leads to particularly good binding of the particles into the cured dental material. Particular preference is given in this connection to methacryloyl groups.

In some cases, preference is given to a curable dental material of the invention (as described above, preferably as defined above as preferred) wherein 70% by weight or more, preferably 80% by weight or more, of the particulate fillers which form the total amount (B) of the particulate fillers in the curable dental material have been subjected to organic surface modification, the curable dental material preferably comprising exclusively filler particles which have been subjected to organic surface modification. Preferably, these are organic surface modifications as described above and below.

In other cases, preference is given to a curable dental material of the invention wherein component (B1) comprises exclusively organically surface-modified filler particles.

Particular preference is given to a curable dental material of the invention (as described above, preferably as defined above as preferred) wherein the total amount (B) of the particulate fillers in the curable dental material comprises exclusively organically surface-modified particulate fillers. In this case, the curable dental material does not comprise any particulate fillers without organic surface modification. The statements made above and below with regard to curable dental materials of the invention apply correspondingly to curable dental materials of the invention wherein component (B1) comprises exclusively organically surface-modified filler particles (preferably as described above), the curable dental material of the invention preferably comprising exclusively organically surface-modified filler particles (preferably organic surface modifications as described above and below in the text).

Particular preference is given to a curable dental material of the invention (as described above, preferably as defined above as preferred) wherein the total amount (A) of the polymerizable monomer(s) has a refractive index $n_A$ in the range from 1.45 to 1.55, preferably a refractive index $n_A$ in the range from 1.48 to 1.55. The refractive index $n_A$ is preferably determined in the corresponding starting material.

One, more than one or all of the one, two, three or more than three polymerizable monomers which form the total amount (A) of the polymerizable monomers in the curable dental material are preferably light-curable (i.e. photopolymerizable) monomers. These light-curable (i.e. photopolymerizable) monomers are preferably selected from the group consisting of 2-hydroxyethyl methacrylate (HEMA), 2-hydroxypropyl methacrylate and 3-hydroxypropyl methacrylate (HPMA), 1,2-dihydroxypropyl methacrylate, 1,3-dihydroxypropyl methacrylate, 2,3-dihydroxypropyl methacrylate, ethylene glycol dimethacrylate (EGDMA), diethylene glycol dimethacrylate, triethylene glycol dimethacrylate (TEDMA), tetraethylene glycol dimethacrylate (TEGDMA), polyethylene glycol dimethacrylate (PEGDMA), propylene glycol dimethacrylate (PGDMA), dipropylene glycol dimethacrylate, tripropylene glycol dimethacrylate (TPGDMA), tetrapropylene glycol dimethacrylate, polypropylene glycol dimethacrylate (PEGDMA), butane-1,4-diol dimethacrylate, butane-1,3-diol dimethacrylate, hexane-1,6-diol dimethacrylate (HEDMA), dodecane-1,12-diol dimethacrylate (DODMA), 2-hydroxypropyl 1,3-dimethacrylate and 3-hydroxypropyl 1,2-dimethacrylate (GDMA), bisphenol A glycerolate dimethacrylate (bis-GMA), ethoxylated bisphenol A dimethacrylate (bis-EMA), 7,7,9-trimethyl-4,13-dioxo-5,12-diazahexadecane 1,16-dioxydimethacrylate (UDMA), neopentyl glycol dimethacrylate, trimethylolpropane trimethacrylate (TMPTMA), pentaerythritol dimethacrylate and dimethacrylates of dihydroxymethyltricyclo[5.2.1.0$^{2,6}$]decane, such as tricyclodecanedimethanol dimethacrylate (TCD-DMA).

Particular preference is given in some cases to the dimethacrylates or diacrylates of dihydroxymethyltricyclo [5.2.1.0$^{2,6}$]decane, as described in publications DE 2419887 A1, DE 2406557 A1, DE 2931926 A1, DE 3522005 A1, DE 3522006 A1, DE 3703120 A1, DE 102005021332 A1, DE 102005053775 A1, DE 102006060983 A1, DE 69935794 T2 and DE 102007034457 A1, which form part of the present application by way of reference.

In addition, it is also possible to use light-curable monomers having ethylenic double bonds and based on polysiloxanes, as described, for example, in DE 19903177 A1 or in DE 4416857 C1, which are part of the present application by way of reference.

Further preferred polymerizable monomers have one or more acid functions.

Suitable monomers containing a phosphoric acid group are, for example, 2-(meth)-acryloyloxyethyl dihydrogenphosphate, bis[2-(meth)acryloyloxyethyl]hydrogenphosphate, 2-(meth)acryloyloxyethylphenyl hydrogenphosphate, 6-(meth)acryloyloxyhexyl dihydrogenphosphate, 10-(meth) acryloyloxydecyl dihydrogenphosphate (MDP), 6-(meth)-acryloyloxyhexylphenyl hydrogenphosphate, 10-(meth) acryloyloxydecyl dihydrogenphosphate, 1,3-di(meth) acryloyloxypropane 2-dihydrogenphosphate, 1,3-di(meth)- acryloyloxypropane 2-phenyl hydrogenphosphate and bis[5-(2-(meth)acryloyloxyethoxy-carbonyl)heptyl] hydrogenphosphate.

Suitable monomers containing a carboxylic acid group are, for example, 4-(meth)-acryloyloxyethyltrimellitic acid (4-MET), 4-(meth)acryloyloxyethyltrimellitic anhydride (4-META), 4-(meth)acryloyloxydecyltrimellitic acid, 4-(meth)acryloyloxydecyltrimellitic anhydride, 11-(meth)acryloyloxy-1,1-undecanedicarboxylic acid, 1,4-di(meth)acryloyloxy-pyromellitic acid, 2-(meth)acryloyloxyethyl-maleic acid, 2-(meth)acryloyloxyethylphthalic acid and 2-(meth)acryloyloxyethylhexahydrophthalic acid.

Further suitable monomers bearing acid groups are specified, for example, in EP 0980682 B1 and EP 0948955 A1, which form part of the present application by way of reference.

In selected cases, preference is given to a curable dental material of the invention (as described above, preferably as defined above as preferred) wherein the total amount (A) of the polymerizable monomers in the curable dental material comprises or consists of, preferably comprises, the polymerizable monomer TCD-DMA.

The refractive indices reported in conjunction with the curable dental material of the invention (as described above and below, especially below under the heading "Examples") and the cured dental material of the invention (as described below, especially below under the heading "Examples") relate to a temperature of 20° C. and to light of a wavelength of 589 nm (sodium D line) ($n_D^{20}$).

In in-house studies, it has been found that a refractive index $n_A$ of the total amount (A) of the polymerizable monomer(s) in the range from 1.45 to 1.55 very frequently leads to very good translucence values, since the refractive indices of the one, two, three or more than three fillers which form the total amount (B) of the fillers in the curable dental material can be matched in a comparatively simple manner to such a refractive index $n_A$ (in a corresponding mixture of polymerizable monomers and fillers; further details further down in the text). As a result of this good matching, the light used in light-induced polymerization of polymerizable monomers in the curable dental material achieves a high penetration depth and hence results in homogeneous polymerization. This leads to a high-quality cured dental material (as described below in the text).

If the refractive index $n_A$ is less than 1.45 or greater than 1.55, the aforementioned matching becomes more complex in many cases (especially in the case of a refractive index of less than 1.45), and the penetration depth of the light is acceptable only in a few cases, or is barely acceptable (since particularly intense light scatter is to be expected in most cases). This increases the risk that nonpolymerized polymerizable monomers will escape from an (only partly) cured dental material and migrate into the oral cavity. In addition, such (partly) cured dental materials have a reduced viscosity in many cases. Such curable dental materials then inconveniently have to be applied in very thin layers and each layer has to be cured individually, in order to minimize the aforementioned disadvantages. If the refractive index is greater than 1.45 but less than 1.48, in most cases, sufficiently good matching is achieved, so as to result in sufficiently good penetration depth of the light. Application of such a curable dental material (and the subsequent curing) can then be effected correspondingly without any great difficulty. If the refractive index is within a range from 1.48 to 1.55, very good results are regularly achieved.

Particular preference is given to a curable dental material of the invention (as described above, preferably as defined above as preferred) wherein the total amount of the particulate fillers in component (B1) has a refractive index $n_{B1}$ in the range from 1.55 to 1.64.

In-house studies have shown that a curable dental material of the invention (as described above, preferably as defined above as preferred) leads to very good results in DVT studies which have been conducted with a cured dental material based on the curable dental material of the invention. As shown by the comparison with noninventive curable dental materials in in-house studies, this is attributable particularly to the presence of the above-described particulate filler particles of ytterbium fluoride and/or barium sulphate.

Barium sulphate has a refractive index of 1.64, ytterbium fluoride 1.55. Thus, the above-described component (B1) has a refractive index $n_{B1}$ in the range from 1.55 to 1.64. If component (B1) consists of barium sulphate, component (B1) has a refractive index $n_{B1}$ of 1.64 (the refractive index of component (B1) in this case corresponds to the refractive index of barium sulphate). If component (B1) consists of ytterbium fluoride, component (B1) has a refractive index $n_{B1}$ of 1.55 (the refractive index of component (B1) in this case corresponds to the refractive index of ytterbium fluoride) (for determination of the refractive index see below in the text under "Examples", point I.a).

Depending on the desired use, in some cases, preference is given to a curable dental material of the invention (as described above, preferably as defined above as preferred) in which a mixture of barium sulphate and ytterbium fluoride is used, where the refractive index of this mixture is preferably in the range from 1.55 to 1.64, more preferably in the range from 1.55 to 1.60. The refractive index of such a mixture can be determined as described below under "Examples", point I.a.

The refractive index of component (B1) is important since this refractive index affects the refractive index of the curable dental material (in this regard, see further down in the text). In order to achieve high translucence in the curable dental material (and hence an accompanying good penetration depth of the light for polymerization of polymerizable monomers in the curable dental material), exact determination or exact knowledge of the individual refractive indices is important.

Particular preference is given to a curable dental material of the invention (as described above, preferably as defined above as preferred) wherein the proportion of component (B1) is within a range from 2.5% by weight to 20% by weight, preferably within a range from 5% by weight to 18% by weight, further preferably within a range from 10.1% by weight to 18% by weight, more preferably within a range from 10.1% by weight to 16% by weight, based on the total mass of the curable dental material.

In in-house studies, it has been found that x-ray-opaque filler particles as defined above for component (B1), in a curable dental material of the invention (as described above, preferably as defined above as preferred), lead to good results in DVT images. More particularly, a reduced number of artefacts has been observed in corresponding DVT images, as compared with DVT images which, under otherwise identical imaging conditions, show test specimens having a composition not corresponding to the composition of curable dental materials of the invention, especially those test specimens which do not comprise any filler particles as defined above in the text for component (B1).

Typical artefacts in DVT images are considered to be (an exact elucidation of the artefacts can be found in following article: R. Schulze et al., "Artefacts in CBCT: a review", Dentomaxillofacial Radiology, 40, 265-273 (2011)):
- beam hardening artefacts,
- extinguishment artefacts,
- ring artefacts,
- movement artefacts,
- alias artefacts,
- partial volume effects/"exponential edge gradient" effects,
- general artefacts such as
  - scatter,
  - noise,
  - local tomography.

If the proportion of component (B1) is within a range from 2.5% by weight to 20% by weight, based on the total mass of the curable dental material, comparatively good results are regularly gained, i.e. the number of artefacts and the distortion by artefacts in DVT images is regularly reduced. If the proportion of component (B1) is within a range from 5% by weight to 18% by weight, particularly good results are regularly achieved, i.e. a particularly good reduction in artefacts. If the proportion of component (B1) is within a range from 10.1% by weight to 18% by weight, based on the total mass of the curable dental material, very good results are regularly achieved, i.e. a regular, very good reduction in artefacts. In some cases, it is preferable that the proportion of component (B1) is within a range from 10.1% by weight to 16% by weight, based on the total mass of the curable dental material. In these cases too, very good results are regularly achieved, i.e. a very good reduction in artefacts.

If the proportion of component (B1) is below a value of 2.5% by weight, it is regularly the case that (i) no good/satisfactory reduction in artefacts and (ii) no satisfactory x-ray opacity are achieved (especially in the absence of sufficient amounts of other x-ray-opaque particulate fillers). These effects are enhanced with the extent to which the proportion of component (B1) is below the value of 2.5% by weight.

If the proportion of component (B1) exceeds a value of 20% by weight, it is regularly the case that a consistency not having good processability is observed in the curable dental material of the invention, as is an impairment in the properties of strength, hardness and abrasion resistance of a cured dental material of the invention produced therefrom.

Particular preference is given to a curable dental material of the invention (as described above, preferably as defined above as preferred) wherein the total amount (B) of the particulate fillers (as defined above) consists of component (B1) and component (B2) (as defined above), where the total amount of the particulate fillers in component (B2) preferably has a refractive index $n_{B2}$ in the range from 1.49 to 1.62, more preferably in the range from 1.50 to 1.56.

As explained, all filler particles that cannot be allotted to component (B1) are allotted to component (B2). Preferred fillers of component (B2) and one, two or more than two fillers selected from the group consisting of inorganic fillers and organic fillers, with the following proviso: fillers of component (B2) are not fillers of component (B1) and do not include any fillers of component (B1).

Preferred inorganic fillers for use as constituent of component (B2) are selected from the group consisting of amorphous materials based on $SiO_2$, $ZrO_2$ and/or $TiO_2$, mixed oxides, fumed silica, precipitated silica, barium silicate glasses, barium fluorosilicate glasses, strontium silicate glasses, strontium fluorosilicate glasses and other dental glasses, quartz glass, Li/Al silicate glasses, calcium silicates, sodium aluminium silicates, fluoroaluminium silicate glasses, feldspar, oxides of aluminium or silicon, zeolites, apatite, zirconium silicates and sparingly soluble metal salts such as calcium fluoride. Particularly preferred inorganic filler particles for use as constituent of component (B2) are dental glasses, for example from Schott, the refractive indices of which are in the range from 1.49 to 1.62, more preferably in the range from 1.50 to 1.56. Very particularly preferred dental glasses from Schott bear the names GM27884 and G018-186.

Preference is given to the use of surface-modified inorganic filler particles (inorganic filler particles as described above, preferably as defined above as preferred). Preferred surface-modified inorganic filler particles are obtained by surface modification with a silane, preferably by surface modification with gamma-methacryloyloxypropyltrimethoxy-silane.

In some cases, it is possible, for example, to use reinforcing filler materials such as glass fibres, polyamide fibres or carbon fibres. A curable dental material of the invention may also contain finely divided slivers or bead polymers, where the bead polymers may also be homo- or copolymers of organic curable monomers.

Preferred organic fillers for use as constituent of component (B2) comprise or consist of, for example, one or more compounds selected from the group consisting of polyvinylacetate and copolymers of polyvinylacetate with one or more polymerizable compounds, polystyrene, polyethylene, polypropylene, waxes such as polyethylene wax, polybutylene, polybutadiene, copolymers of butadiene and of styrene, polyacrylonitriles, resins such as rosin or hydrocarbon resins, poly(meth)acrylate esters, i.e. reaction products of poly(meth)acrylic acid with linear or branched aliphatic, aromatic or cycloaliphatic alcohols such as methanol, ethanol, propanol, isopropanol, the isomeric butanols and higher homologues of the alcohols mentioned having up to 22 carbon atoms, cyclohexanol, benzyl alcohol and the like, polydialkylmaleates such as dibutyl maleate and copolymers thereof and polymers containing silyl groups, such as polyvinylsilanes or copolymers of vinylsilane with one or more of the monomers mentioned.

Particular preference is given to a curable dental material of the invention (as described above, preferably as defined above as preferred) wherein the proportion of the total amount (A) is in the range from 7.95% to 27.95% by weight, preferably in the range from 9% to 24.9% by weight, based on the total mass of the starting materials to be mixed.

If the proportion of the total amount (A) is in the range from 7.95% to 27.95% by weight, based on the total mass of the starting materials to be mixed, the curable dental material of the invention (as described above, preferably as defined above as preferred) regularly has good processability in the production of the cured dental material of the invention (as described above, preferably as defined above as preferred). A cured dental material produced therefrom also regularly has good mechanical properties, for example very good strengths, hardnesses and abrasion resistances. If the value is (well) below 7.95% by weight, the end result is not a pasty dental material having pleasant or easy processibility. In some cases, it has even been observed that such a dental material was not processible at all.

If the proportion of the total amount (A) is (much) greater than 27.95% by weight, this leads in many cases to cured dental materials which do not have sufficient strength, hardness and abrasion resistance.

The curable dental material of the invention is preferably a dental material having a high filler level. Particular preference is given to a curable dental material of the invention (as described above, preferably as defined above as preferred) wherein the proportion of the total amount (B) is in the range from 72% to 92% by weight, preferably in the range from 75% to 89.5% by weight, based on the total mass of the starting materials to be mixed.

If the proportion of the total amount (B) is in the range from 72% to 92% by weight, based on the total mass of the starting materials to be mixed, the cured dental material of the invention that results from polymerization of polymerizable monomers in the curable dental material in most cases has very good abrasion resistance, strength and hardness. Particularly good abrasion resistance, strength and hardness are regularly the result whenever the proportion of the total amount of (B) is 75% by weight or greater, based on the total mass of the starting materials to be mixed.

If the proportion of the total amount (B) is (much) less than 72% by weight, inadequate abrasion resistance has been observed in individual cases.

If the proportion of the total amount (B) (far) exceeds the 92% by weight, there is a corresponding fall in the proportion of polymerizable monomers in the curable dental material of the invention, and it is regularly so low that the end result is not a pasty dental material having pleasant or easy processibility. In some cases, it has even been observed that such a dental material was not processible at all.

Particular preference is given to a curable dental material of the invention (as described above, preferably as defined above as preferred) wherein the proportion of the total amount (C) is in the range from 0.05% to 2% by weight, preferably in the range from 0.1% to 1.5% by weight, based on the total mass of the starting materials to be mixed.

The total amount (C) preferably consists of one of, more than one of or all the compounds selected from the group consisting of
rheological auxiliaries,
polymerization initiators, preferably photoinitiators,
chemical compounds as catalysts or constituents of catalyst systems,
colourants,
stabilizers, especially UV and daylight stabilizers,
inhibitors,
activators,
molecular weight regulators,
preservatives,
interface-active substances,
biocides, preferably bactericides,
organic polymers and oligomers and compounds having high molecular weights, preferably plasticizers,
thickeners and
dental medicaments.

Particularly preferred auxiliaries are polymerization initiators, preferably photoinitiators, colourants and inhibitors. The rule here is that substances should be regarded as a constituent of the total amount (C) when they do not meet the definitions of (A) and (B), i.e. are neither a polymerizable monomer nor a particulate filler. Colour pigments, for example, are of course colourants, but are allotted to component (B) because they can also be regarded as particulate filler.

Preferred curable dental materials of the invention (as defined above, preferably as defined above as preferred) are light-curable (photocurable). In that case, the polymerization of polymerizable monomers is regularly effected by the action of light of particular wavelengths and in the presence of photoinitiators. Examples of a photoinitiator include compounds which have merely photosensitizing action, and combinations of photosensitizer and accelerator.

Examples of photosensitizers are alpha-diketones, benzoin alkyl ethers, thioxanthones, benzophenones, acylphosphine oxides, acetophenones, ketals, titanocenes, sensitizing dyes, etc. The sensitizers may be employed alone or in combination. Specific examples of the different classes can be found, for example, in DE 10 2006 019 092 A1 or in DE 39 41 629 C2, which form part of the present application by way of reference.

Examples of accelerators which are used together with sensitizers are tertiary amines, secondary amines, barbituric acids, tin compounds, aldehydes and sulphur compounds. Specific examples of the different classes can be found in DE 10 2006 019 092 A1 or in DE 39 41 629 C2, which form part of the present application by way of reference.

Further suitable initiators and initiator combinations are described in DE 601 16 142 T2, which forms part of the present application by way of reference.

Preferred photoinitiators in the context of the present invention are characterized in that they can bring about the curing (polymerization) of a curable dental material of the invention or to be employed or used in accordance with the invention through absorption of light in the wavelength range from 300 nm to 700 nm, preferably from 350 nm to 600 nm and more preferably from 380 nm to 500 nm, optionally in combination with one or more coinitiators.

In individual cases, preference is given to a curable dental material of the invention (as defined above, preferably as defined above as preferred) which is curable by chemical curing. For this purpose, the person skilled in the art is aware of various initiators for chemical curing. In this regard, reference is made by way of example to the disclosure in EP 1 720 506 A1.

In many cases, preference is given to a curable dental material of the invention which is both light-curable and chemically curable. These preferred dual-curing dental materials comprise a combination of photoinitiators and initiators for chemical curing. The details above with regard to preferred initiators apply correspondingly.

Preferred light-curable dental materials of the invention (as defined above, preferably as defined above as preferred, including the dual-curing dental materials of the invention) preferably comprise one or more inhibitors (also called stabilizers). These are typically added in order to avoid spontaneous polymerization. They react with prematurely formed free radicals, which are scavenged, so as to prevent premature polymerization. This increases the storage stability of the preferred light-curing dental materials (or the dual-curing dental materials). Inhibitors for use with preference are phenol derivatives such as hydroquinone monomethyl ether (MeHQ) or 2,6-di-tert-butyl-4-methylphenol (BHT). Further inhibitors for use with preference such as tert-butylhydroxyanisole (BHA), 2,2-diphenyl-1-picrylhydrazyl radicals, galvinoxyl radicals, triphenylmethyl radicals, 2,2,6,6-tetramethylpiperidinyl-1-oxyl radicals (TEMPO) and derivatives of TEMPO or phenothiazine and derivatives of this compound are described in EP 0 783 880 B1, which forms part of the present application by way of reference. Alternative inhibitors are specified in DE 101 19 831 A1 and in EP 1 563 821 A1, which form part of the present application by way of reference.

Preferred curable dental materials of the invention (as defined above, preferably as defined above as preferred) have characteristic colours, preferably a tooth colour covered by the "VITA classical A1-D4 colour scale"; such colours are referred to as A1-A4 (reddish-brownish), B1-B4 (reddish-yellowish), C1-C4 (grey shades), D2-D4 (reddishgrey). Preferred colours can be established by means of colourants, preferably colour pigments.

Standard molecular weight regulators are, for example, aldehydes and ketones, such as formaldehyde, acetaldehyde, propionaldehyde, n-butyraldehyde, isobutyraldehyde, methyl ethyl ketone, acetone, methyl isobutyl ketone, formic acid, ammonium formate, hydroxyammonium sulphate and hydroxyammonium phosphate, compounds containing sulphur in organically bound form, such as di-n-butyl sulphide, di-n-octyl sulphide, diphenyl sulphide, diisopropyl disulphide, di-n-butyl disulphide, di-n-hexyl disulphide, diacetyl disulphide and di-tert-butyl trisulphide, compounds containing sulphur in the form of SH groups, such as n-butyl mercaptan, n-hexyl mercaptan and n-dodecyl mercaptan, octadecyl mercaptan, further sulphur compounds such as hydrogensulphites, disulphites, compounds such as mercaptoethanol, mercaptobutanol, mercaptoacetic acid, 3-mercaptopropionic acid, mercaptosuccinic acid, thioglycerol, thioglycolic acid, diethanol sulphide, thiodiglycol, ethylthioethanol, 2,2,4,6,6-pentamethylheptane-4-thiol, 2,2,4,6,6,8,8-heptamethylnonane-4-thiol, thiourea, dimethyl sulphoxide, ethylhexyl thio-glycolate, pentaerythritol tetrathioglycolate, mercaptopropyltrimethoxysilane, then allyl compounds such as allyl alcohol, allyl bromide, or benzyl compounds such as benzyl chloride or alkyl halides such as chloroform, bromotrichloromethane or tetrachloromethane, tetrabromomethane, methylene chloride, and also lower and higher molecular weight, monohydric or polyhydric alcohols such as methanol, ethanol, n-propanol, isopropanol, tert-butanol, sec-butanol, n-butanol, amyl alcohol, cyclohexanol, octanol, dodecanol, 1-ethylhexanol, glycerol, stearyl alcohol, oleyl alcohol, hydroxyethyl methacrylate or amines such as triethylamine, and toluene or ethylbenzene.

Further, and in many cases preferred, molecular weight regulators are, for example, various terpenes, especially terpinenes (α-terpinene, β-terpinene, γ-terpinene), phellandrenes (α-phellandrene, β-phellandrene) and terpinolene (also called δ-terpinene), 1,4-cyclohexadiene (optionally substituted), 1,3-cyclohexadiene (optionally substituted), 1,4-dihydronaphthalene, 1,4,5,8-tetrahydronaphthalene, 2,5-dihydrofuran or dimeric α-styrene (2,4-diphenyl-4-methyl-1-pentene), and linoleic acid and α-linolenic acid.

As already described above, good x-ray opacity of the curable dental material of the invention or of the cured dental material of the invention is necessary for a high-contrast representation in conventional x-ray images and DVT images (for determination of x-ray opacity see below under "Examples", point I.b). Particular preference is given to a curable dental material of the invention (as described above, preferably as defined above as preferred) wherein:
the curable dental material has an x-ray opacity of 3.5 mm Al (equivalent to 350% Al) or greater
and/or
by polymerization of polymerizable monomers in the curable dental material it is possible to obtain a cured dental material having an x-ray opacity of 3.5 mm Al (equivalent to 350% Al) or greater.

An x-ray opacity in mm Al is calculated as follows:

x-ray opacity [mm Al]=$(d_{Al}/d_P)$ where $d_{Al}$ is the thickness in mm of an aluminium wedge at which identical blackening occurs to that for the test specimen, $d_P$ is the test specimen thickness of the curable dental material of the invention or of the cured dental material of the invention in mm.

An x-ray opacity of 3.5 mm Al means that the quotient of $d_{Al}$ and $d_P$ is 3.5, meaning that, with identical blackening, the thickness of the aluminium wedge is 3.5 times the thickness of the test specimen. If, for example, the thickness $d_P$ of a test specimen is 1 mm and the thickness $d_{Al}$ of a corresponding aluminium wedge is 3.5 mm, the x-ray opacity is 3.5 mm (or 350%). A high value of mm Al (or percent Al) thus means a high x-ray opacity.

Preferably, the x-ray opacity is determined on the cured dental material of the invention (as described above and especially as described below, preferably as described above and especially as described below as preferred). Thus, preference is given to a cured dental material of the invention having an x-ray opacity of 3.5 mm Al or greater, preferably 4.0 mm Al or greater.

In-house studies have shown that a curable dental material of the invention, preferably a cured dental material of the invention obtainable therefrom by polymerization of polymerizable monomers and having an x-ray opacity of 3.5 mm Al or greater, has led in very many cases to very good results in conventional x-ray images. More particularly, because of the high x-ray opacity, a very good contrast was observed between synthetic dental material and natural tooth material in these images. These studies have also shown that such a curable (or cured) dental material of the invention, likewise regularly leads to very good results in DVT images. Because of the high x-ray opacity and the composition of the curable dental material of the invention, in these DVT images, very good contrasts were firstly observed between synthetic dental materials and natural tooth materials, and secondly barely any artefacts were observed.

If the x-ray opacity is (well) below the limit of 3.5 mm Al, in a few cases, a sufficient contrast between synthetic dental material and natural tooth material was observed in DVT images in a few cases, but there were isolated instances of increasing levels of artefacts (especially with falling x-ray opacity).

As already mentioned above, it is desirable for the curable dental material of the invention (as described above, preferably as defined above as preferred) to have high translucence. The effect of a high translucence is that the light required for polymerization of polymerizable monomers can also penetrate into deeper layers of a preparation composed of a curable dental material of the invention (good penetration depth). Only in this way is it assured that the light required will also reach deeper-lying layers of polymerizable monomers and lead to homogeneous curing.

In the assessment of translucence, the practitioner, when designing curable dental materials, will frequently be guided by a partial mixture which is already similar to the final product (for example to a curable dental material of the invention) and has very high translucence. Such a partial mixture typically does not contain any of the particulate dyes that are familiar to the person skilled in the art and are used customarily in practice, nor any other colourants (i.e. dyes and colourants which are used for the alteration of the colour or shade). Typically, partial mixtures of this kind (or cured partial mixtures that result from polymerization of polymerizable monomers in the partial mixture) have a translucence of 45% or greater, preferably of 50% or greater (for the determination of translucence see point I.c under "Examples" further down in the text).

Proceeding from the partial mixture having very high translucence, after addition of selected/specific particulate dyes and/or colourants, a resulting curable dental material of the invention (or a cured dental material of the invention) has defined shades or colours. Such preferred dental materials of the invention (curable or cured) regularly have somewhat reduced translucence compared to the partial mixture, i.e. compared to a dental material of otherwise identical composition except that no particulate dyes and colourants have been added thereto. A reduction in translucence which can be brought about in a controlled manner allows provision of a dental material of the invention for specific applications (for example as dentine substitute: 10% translucence, universal shade: 20% translucence, enamel substitute: 30% translucence, incisal edge: 40% translucence).

Preferably, the translucence is determined on the cured partial mixture (as described above).

In very many cases (both for the aforementioned partial mixture and for a curable dental material of the invention), if the translucence is (well) below 45%, a (distinct) extension of the exposure time will regularly be necessary in order to achieve full curing. It will be clear to the person skilled in the art that the degree of polymerization depends on the exposure time (light having a suitable wavelength). Alternatively, in such cases, it may be necessary to apply a dental material layer by layer, in which case each of these comparatively thin individual layers is cured separately (in which case the curing of these thin individual layers can in turn be effected very quickly). The respective individual layers bind to one another in the course of curing, such that a unit of a cured dental material is finally present.

If the translucence is comparatively high (for example much greater than 50%), the necessary exposure time is shortened correspondingly.

In in-house studies, it has been found that a good penetration depth of the light in the curable dental material of the invention (or in the (partly) cured dental material of the invention) is regularly achieved whenever the refractive index $n_A$ and the refractive index $n_{B2}$ are close to one another (for further details see further down in the text).

For the total amount of the filler particles in component (B1) composed of
 (a) nonaggregated and nonagglomerated filler particles having a particle size in the range from 25 to 120 nm of ytterbium fluoride
 and
 (b) nonaggregated and nonagglomerated filler particles having a particle size in the range from 25 to 120 nm of barium sulphate,
it is generally the case that these have a particle size smaller than half the wavelength of visible light (wavelength of visible light: about 380 nm to 780 nm). This property appears to be very advantageous. In-house studies indicate that the filler particles of component (B1) having the aforementioned particle sizes (and having the refractive indices that corresponds to these filler particles) interact in an advantageous manner with the polymerizable monomers of the total amount (A). A mixture of the polymerizable monomers of the total amount (A) and the filler particles of component (B1) regularly shows negligible light scattering, if any at all, meaning that the translucence of such a mixture is regularly not worsened as a result of presence of the filler particles of component (B1). In spite of this, a distinct improvement in x-ray opacity is achieved. The aforementioned mixture of polymerizable monomers of the total amount (A) and the filler particles of component (B1) regularly has a higher refractive index (referred to hereinafter simply as "modified refractive index") than the polymerizable monomers of the total amount (A) alone (especially when the filler particles of component (B1) comprise ytterbium fluoride). This modified refractive index of such a mixture, in practice, allows selection (and addition) of dental glasses which have comparatively high refractive indices but are nevertheless very close to the modified refractive index. Curable dental materials of the invention which exploit this principle regularly have firstly very good translucence (because the refractive indices are very close to one another) and very good x-ray opacity (because of the filler particles of component (B1) and optionally additional x-ray-opaque dental glasses). Preference is given to a curable dental material of the invention (as described above, preferably as defined above as preferred) having a refractive index $n_{curable}$ in the range from 1.50 to 1.559.

As well as the dental glasses already mentioned above, the total amount (B) may comprise one or more compounds from a multitude of further inorganic particulate fillers. In isolated cases, preference is given to a curable dental material of the invention (as described above, preferably as defined above as preferred) wherein the starting materials to be mixed comprise silicon dioxide in a total amount of less than 0.1% by weight, based on the total mass of the starting materials to be mixed, and preferably comprise no silicon dioxide at all.

The x-ray-opaque properties of a curable dental material of the invention (as described above, preferably as defined above as preferred) are preferably achieved by virtue of the filler particles of component (B1). Particular preference is given to a curable dental material of the invention (as described above, preferably as defined above as preferred) wherein the particulate fillers which form the total amount (B) of the particulate fillers in the curable dental material contain no
 (a) nonaggregated and nonagglomerated filler particles having a particle size in the range from 25 to 120 nm of organically surface-modified ytterbium fluoride
 or contain no
 (b) nonaggregated and nonagglomerated filler particles having a particle size in the range from 25 to 120 nm of organically surface-modified barium sulphate,
and preferably contain no
 (a) nonaggregated and nonagglomerated filler particles having a particle size in the range from 25 to 120 nm of ytterbium fluoride
 or contain no
 (b) nonaggregated and nonagglomerated filler particles having a particle size in the range from 25 to 120 nm of barium sulphate.

In these cases, component (B1) has either a refractive index $n_{B1}$ of 1.55 (ytterbium fluoride) or 1.64 (barium sulphate). The curable dental material of the invention, however, always comprises at least one of the two aforementioned particulate fillers which have nonaggregated and nonagglomerated filler particles and have a particle size in the range from 25 to 120 nm.

In some cases, preference is given to a curable dental material of the invention (as described above, preferably as defined above as preferred) wherein component (B1) consists only of nonaggregated and nonagglomerated filler particles having a particle size in the range from 25 to 120 nm of (preferably organically surface-modified) ytterbium fluoride. In this case, component (B1) has a refractive index $n_{B1}$ of 1.55. As already stated above, the refractive index $n_A$ of the polymerizable monomers is preferably in the range from 1.45 to 1.55; the refractive index $n_{B2}$ of component (B2) (e.g. dental glasses) is preferably in the range from 1.49 to 1.62. In a curable dental material of the invention, it is particularly desirable in principle for the refractive index $n_A$ and the refractive index $n_{B2}$ to be particularly close to one another. As likewise already described above, the refractive index of a mixture of polymerizable monomers of the total amount (A) and the filler particles of component (B1) is affected (altered) by the presence of the filler particles of component (B1) as compared with the refractive index $n_A$ of the polymerizable monomers of the total amount (A). If, for example, the refractive index $n_A$ of the polymerizable monomers is 1.52 and the refractive index $n_{B2}$ of the dental glasses is 1.55, it is advantageous, for example, to match the refractive indices by using ytterbium fluoride having a refractive index of 1.55. If, in contrast, the refractive index $n_A$ is 1.48 and the refractive index $n_{B2}$ 1.61, it is advantageous, for example, to match the refractive indices by using barium sulphate having a refractive index of 1.64.

Particular preference is given to a curable dental material of the invention (as described above, preferably as defined above as preferred) wherein the total amount of component (B1) consisting of the following that are present in the curable dental material:
(a) nonaggregated and nonagglomerated filler particles having a particle size in the range from 25 to 120 nm of ytterbium fluoride
and
(b) nonaggregated and nonagglomerated filler particles having a particle size in the range from 25 to 120 nm of barium sulphate
includes nonaggregated and nonagglomerated filler particles of ytterbium fluoride having a particle size in the range from 30 to 100 nm, preferably in the range from 30 to 80 nm, more preferably in the range from 30 to 60 nm, especially preferably in the range from 35 to 55 nm,
and/or
includes nonaggregated and nonagglomerated filler particles of barium sulphate having a particle size in the range from 30 to 100 nm, preferably in the range from 30 to 80 nm, more preferably in the range from 30 to 60 nm, especially preferably in the range from 35 to 55 nm.

Preferably, the statements made above with regard to curable dental materials of the invention or with regard to cured dental materials of the invention apply correspondingly in conjunction with the aforementioned preferred and particularly preferred particle sizes.

In in-house studies, it has been found that the filler particles of component (B1) (as described above, preferably as defined above as preferred) regularly lead firstly to very good x-ray opacity and secondly to very good translucence. According to in-house studies, particularly good results were regularly achieved when component (B1) comprises filler particles having a particle size in the range from 30 to 80 nm (especially in the range from 30 to 60 nm) (this applies in most cases both to filler particles of ytterbium fluoride and to filler particles of barium sulphate). A curable dental material of the invention comprising such filler particles, or a cured dental material of the invention produced therefrom by polymerization of polymerizable monomers, leads in many cases to a distinct reduction in artefacts in DVT images. Very good results are likewise regularly achieved when component (B1) comprises filler particles having a particle size in the range from 35 to 55 nm. More particularly, filler particles of component (B1) having the aforementioned preferred and particularly preferred particle sizes regularly lead to curable dental materials of the invention having very good consistencies, and so processibility is very good.

In-house studies have shown that, in some cases, the number of artefacts in DVT images increases when the particle size is within a range (well) below 25 nm (cf. Examples below in the text). In addition, it has been observed in some cases that the resulting dental material then no longer has satisfactory consistency.

In-house studies have likewise shown that the translucence in some cases is no longer satisfactory when the particle size (far) exceeds 120 nm.

Particular preference is given to a curable dental material of the invention (preferably as described above, more preferably as defined above as preferred) producible by mixing starting materials, wherein the starting materials to be mixed are exclusively:
in a total amount in the range from 7.95% to 27.95% by weight, based on the total mass of the starting materials to be mixed, one, two, three or more than three polymerizable monomers which form the total amount (A) of the polymerizable monomers in the curable dental material and where the total amount (A) of the polymerizable monomer(s) has a refractive index $n_A$ within a range from 1.45 to 1.55,
in a total amount in the range from 72% to 92% by weight, based on the total mass of the starting materials to be mixed, one, two, three or more than three particulate fillers which form the total amount (B) of the particulate fillers in the curable dental material,
in a total amount in the range from 0.05% to 2% by weight, based on the total mass of the starting materials to be mixed, one, two, three or more than three auxiliaries which form the total amount (C) of the auxiliaries in the curable dental material,
wherein
the curable dental material comprises a component (B1) which forms part of the total amount (B), consisting of the total amount of the following that are present in the curable dental material:
(a) nonaggregated and nonagglomerated filler particles having a particle size in the range from 25 to 120 nm of ytterbium fluoride
where component (B1) preferably comprises, preferably to an extent of more than 50% by weight, nonaggregated and nonagglomerated filler particles of ytterbium fluoride having a particle size in the range from 30 to 100 nm, more preferably in the range from 30 to 80 nm, especially preferably in the range from 30 to 60 nm, most preferably in the range from 35 to 55 nm
and
(b) nonaggregated and nonagglomerated filler particles having a particle size in the range from 25 to 120 nm of barium sulphate,
where component (B1) preferably comprises, preferably to an extent of more than 50% by weight, nonaggregated and nonagglomerated filler particles of barium sulphate having a particle size in the range from 30 to 100 nm, more preferably in the range from 30 to 80 nm, especially preferably in the range from 30 to 60 nm, most preferably in the range from 35 to 55 nm,
wherein
the proportion of component (B1) is
2.5% by weight or greater than 2.5% by weight, preferably within a range from 2.5% by weight to 20% by weight, more preferably within a range from 5% by weight to 18% by weight, further preferably within a range from 10.1% by weight to 18% by weight, more preferably within a range from 10.1% by weight to 16% by weight, based on the total mass of the curable dental material and
90% by weight or greater than 90% by weight, based on the total mass of filler particles of ytterbium fluoride and barium sulphate in the curable dental material
and
the total amount of the particulate fillers in component (B1) preferably has a refractive index $n_{B1}$ in the range from 1.55 to 1.64.

The present invention also relates to a curable dental material of the invention (as described above, preferably as defined above as preferred) for use in a method for treatment of the human or animal body by surgery or therapy and/or in a diagnostic method practiced on the human or animal body (also designated as curable dental material for use in a method for treatment of the human body by therapy and/or in a diagnostic method),
preferably for specific use
in a method of therapy of temporary or permanent filling of a dental cavity,
wherein said dental cavity is preferably selected from the group consisting of cavities in the enamel of a tooth, cavities in the cementum of a tooth, cavities in the dentin of a tooth crown and cavities in form of a blind hole in the dentin of a tooth root (remark: the term "dental cavity" is routinely not used by a person skilled in the art to describe the root canal of a tooth; correspondingly the specific use of the invention does not regard filling of a root canal of a tooth), or
in a method of therapy as
tooth filling material,
dental cement,
dental lining material,
as free-flowing composite material (flow material),
as crown material,
as inlay and/or onlay,
as bridge material
and/or as core build-up material.

As described above, it is possible by polymerization (preferably as described above) of polymerizable monomers (preferably as described above) in a curable material of the invention (as described above, preferably as defined above as preferred) to obtain a cured dental material of the invention. Thus, the present invention also relates to a cured dental material obtainable by polymerizing polymerizable monomers in a curable dental material of the invention (as described above, preferably as defined above as preferred).

The statements made above with regard to the curable dental material of the invention apply correspondingly to the cured dental material of the invention.

The present invention also relates to the use of a curable dental material of the invention (as described above, preferably a curable dental material as defined above as preferred) or a cured dental material of the invention (as described above, preferably a cured dental material as defined above as preferred) for production of a dental product, wherein the production is not effected on the human or animal body, preferably for production of a dental product selected from the group consisting of artificial teeth, inlays, onlays, crowns, bridges, mill blanks, implants and dentures.

In addition, the curable dental materials of the invention can be used in an excellent manner for additive manufacturing methods from the category of rapid prototyping/rapid manufacturing (called rapid product development). These methods generally begin with a digital three-dimensional survey of the oral situation by a 3D scan (chairside: intraoral or labside: extraoral), in order to manufacture subsequently a dental product (also called dental moulding) on the basis of the CAD data generated. In this case, dental products are produced by gradual layer buildup from liquid to pasty curable dental materials, preferably from curable dental materials of the invention, for example by 3D printing, stereolithography, digital light processing, etc. Dental products, such as inlays, onlays, crowns, bridges, temporary prostheses and orthodontic products, can be manufactured (i) directly on site in the dental practice, (ii) without any great time demands or preparative complexity and (iii) without high material loss. For production of dental products of this kind by means of stereolithography methods, liquid or pasty radiation-curable dental materials are used, preferably corresponding curable dental materials of the invention, as described above. Layer-by-layer curing is achieved by point exposure or selective exposure by means of a mask system with actinic radiation.

Particular preference is given to the use of a curable dental material of the invention (as described above, preferably a curable dental material as defined above as preferred) as construction material in an additive manufacturing method that uses a digital data model, preferably in a 3D printing method, preferably for production of a dental product, preferably for production of a dental product selected from the group consisting of artificial teeth, inlays, onlays, crowns, bridges, mill blanks, implants and dentures. Such production of dental products is of course not effected on the human or animal body.

The present invention also relates to a method for producing a dental product by means of an additive manufacturing method that uses a digital data model, comprising the steps of:
producing or providing a curable dental material of the invention (as described above, preferably a curable dental material as defined above as preferred), preferably producing by a method of the invention as described hereinafter (preferably as defined hereinafter as preferred),
processing the curable dental material produced or provided in the additive manufacturing method that uses a digital data model, so as to result in the dental product or a precursor of the dental product,
wherein the dental product is preferably selected from the group consisting of artificial teeth, inlays, onlays, crowns, bridges, mill blanks, implants and dentures.

The processing of the produced or provided curable dental material in the additive manufacturing method that uses a digital data model is preferably conducted in a manufacturing chamber of an apparatus suitable for conducting said additive manufacturing method.

The present invention also relates to a kit comprising
one or more than one dental syringe
and
(i) one, two or more than two curable dental materials of the invention (as described above, preferably as defined above as preferred)
and/or
(ii) one, two or more than two base pastes and one, two or more than two catalyst pastes, wherein a curable dental material of the invention (as described above, preferably as defined above as preferred) is obtainable by mixing a base paste and the corresponding catalyst paste.

The use of base pastes and catalyst pastes is typically necessary when the kit is to provide a curable dental material of the invention which is (i) chemically curable or (ii) dual-curing.

The person skilled in the art is aware of various initiators for chemical curing (in this respect, reference is made to EP 1 720 506 A1).

Preferred initiators for chemical curing are benzoyl peroxide, lauroyl peroxide, especially dibenzoyl peroxide, in combination with amines such as N,N-dimethyl-p-toluidine, N,N-dihydroxyethyl-p-toluidine, and structurally related amines.

The initiators needed for chemical curing (e.g. peroxides, amines or corresponding combinations of peroxides and amines) are typically divided between appropriate base pastes and catalyst pastes. The mixing of the amine-containing component (base paste) with the peroxide-containing component (initiator or catalyst paste) initiates the free radical reaction through the reaction of amine and peroxide (redox reaction).

Dual-curing systems comprise a combination of photoinitiators and initiators for chemical curing (with regard to photoinitiators, see further up in the text).

For example, the base paste may additionally comprise a photoinitiator, such that the base paste can be used either solely as a light-curing dental composition or, together with the initiator paste, as a light- and self-curing dental composition.

As well as the oxidatively active organic peroxide compounds, redox systems used may also be barbituric acids or barbituric acid derivatives and malonylsulphamides.

Among the barbituric acid systems, the "Bredereck systems" are of high importance, Examples of suitable "Bredereck systems" and references to the corresponding patent literature can be found in EP 1 839 640 A2 and in DE 1 495 520 A1, WO 02/092021 A1 or in WO 02/092023 A1.

Suitable malonylsulphamides are described in EP 0 059 451 A1. Preferred compounds are 2,6-dimethyl-4-isobutyl-malonylsulphamide, 2,6-diisobutyl-4-propylmalonylsulphamide, 2,6-dibutyl-4-propylmalonylsulphamide, 2,6-dimethyl-4-ethylmalonylsulphamide and 2,6-dioctyl-4-isobutylmalonylsulphamide.

In addition, it is possible to use sulphur compounds in the +2 or +4 oxidation state, such as sodium benzenesulphinate or sodium para-toluenesulphinate.

To accelerate the curing, the polymerization can be performed in the presence of heavy metal compounds such as Ce, Fe, Cu, Mn, Co, Sn or Zn, particular preference being given to copper compounds. The heavy metal compounds are preferably used in the form of soluble organic compounds. Preferred copper compounds here are copper benzoate, copper acetate, copper ethylhexanoate, copper di(methacrylate), copper acetylacetonate and copper naphthenate.

The dental syringe(s) is/are suitable for dental purposes, i.e. suitable for applications in the oral cavity.

If a kit of the invention (as described above) comprises one or more base pastes and one or more catalyst pastes, the base paste(s) and the corresponding catalyst paste(s) each constitutes a partial mixture of the above-described starting materials used exclusively. In this case, this means that the above-described mixing of the starting materials is concluded only by mixing a base paste and the corresponding catalyst paste. The result is then a curable dental material of the invention (as defined above, preferably a curable dental material as defined above as preferred).

Preferably, the kit of the invention (as defined above, preferably as described above as preferred) additionally comprises one of, more than one of or all the items selected from the group consisting of:
one, two or more than two adhesives,
one, two or more than two etching gels,
one or more than one shade guide,
one or more than one brush,
one or more than one dental material having a viscosity different from the viscosity/viscosities of the curable dental material(s) of the invention and/or from the viscosity/viscosities of the base paste(s) or the catalyst paste(s), preferably one or more than one flow material.

The statements made above in relation to the curable dental material of the invention and in relation to the cured dental material of the invention apply correspondingly to the use of the curable dental material of the invention and to the use of the cured dental material of the invention, especially to the production of dental products selected from the group consisting of artificial teeth, inlays, onlays, crowns, bridges, mill blanks, implants and dentures and/or to the dental products selected from the group consisting of artificial teeth, inlays, onlays, crowns, bridges, mill blanks, implants and dentures themselves.

The present invention also relates to a method for producing a curable dental material of the invention (as described above, preferably a curable dental material as defined above as preferred), comprising the following steps:
(i) producing or providing the starting materials as defined above (preferably starting materials as preferably defined above as preferred),
or
producing or providing partial mixtures from the starting materials as defined above (preferably starting materials as preferably defined above as preferred),
(ii) mixing the starting materials produced or provided in (i) or the partial mixtures produced or provided in (i), so as to result in the curable dental material in each case.

The mixing in step (ii) is preferably conducted in a mixing chamber of a mixing apparatus.

The present invention also relates to a method for producing a cured dental material of the invention (as described above, preferably a cured dental material as defined above as preferred) or a dental product as defined above (preferably a dental product as defined above as preferred), comprising the steps of:
(I) producing or providing a curable dental material of the invention (as described above, preferably a curable dental material as defined above as preferred), preferably producing by a method of the invention for producing a curable dental material of the invention (a method as described above, preferably as described above as preferred),
(II) polymerizing polymerizable monomers in the curable dental material, so as to result in the cured dental material.

In addition, the present invention relates to a method for dental treatment of a patient, comprising the following steps:
(1) producing or providing a curable dental material of the invention (as described above, preferably a curable dental material as defined above as preferred)
or
a cured dental material of the invention (as described above, preferably a cured dental material as defined above as preferred),
(2) introducing and positioning the curable dental material produced or provided in the patient's oral cavity and curing the curable dental material (see step (1), first alternative)

or
   introducing and positioning the cured dental material produced or provided in the patient's oral cavity (see step (1), second alternative),
respectively.

The present invention also relates to the use of an amount of
   (a) nonaggregated and nonagglomerated filler particles having a particle size in the range from 25 to 120 nm of ytterbium fluoride
   and
   (b) nonaggregated and nonagglomerated filler particles having a particle size in the range from 25 to 120 nm of barium sulphate
as x-ray-opaque filler in a curable dental material.

The statements made above with regard to a curable/cured dental material of the invention apply correspondingly to the use of the above-defined amount according to the invention. Particular preference is given to the use of an amount of
   (a) nonaggregated and nonagglomerated filler particles having a particle size in the range from 25 to 120 nm of ytterbium fluoride
   and/or
   (b) nonaggregated and nonagglomerated filler particles having a particle size in the range from 25 to 120 nm of barium sulphate
as x-ray-opaque filler in a curable dental material.

The invention is elucidated in detail hereinafter by examples.

EXAMPLES

I. Determination Methods

I.a Determination of the Refractive Indices

Refractive indices were determined at 20° C. and for light of a wavelength of 589 nm (sodium D line). For free-flowing and pasty samples, an analogous AR4 Abbe refractometer from A. Krüss Optronic or a digital RE 40 system from Mettler-Toledo was used.

If a refractive index for pulverulent particulate fillers was not specified by the manufacturer, the refractive index was determined by means of the immersion method. For this purpose, immersion fluids having known refractive indices were used for comparative purposes. The determination was conducted as follows:

In a first step, several individual samples of the filler powder to be analysed were provided on microscope slides. Each of these individual samples, in a second step, was wetted with a specific immersion fluid. The specific immersion fluids differed in terms of their refractive indices. In a third step, the wetted individual samples were examined under a Motic BA 210 LED light microscope and the refractive index was determined by comparison. The refractive index of an individual sample corresponds to the refractive index of an immersion fluid if no phase boundary was apparent under the microscope.

I.b Determination of X-Ray Opacity

The x-ray opacity of cured dental materials was determined to DIN ISO 4049:2010-03 (referred to as x-ray visibility therein) by means of a digital instrument. Each of the samples was exposed at 60 kV and 7 mA for 0.04 s.

I.c Determination of Translucence

Translucence was determined on test specimens of cured dental materials.

The test specimens produced were examined with a Hunterlab ColorFlex EZ 45/0 twin-beam spectrophotometer. The examination was effected under D65 standard light at an observation angle of 10° in reflection mode against a black tile and a white tile. The tristimulus values $Y_{black}$ and $Y_{white}$ were determined and then the opacity in percent was calculated by the formula opacity=$100*Y_{black}/Y_{white}$.

In a third step, the calculated opacity was converted to a translucence by the formula translucence=100 minus opacity.

The test specimens were produced using the curable dental materials defined in Table 1 (cf. additionally the text below for point III.a).

I.d Determination of Particle Sizes

Particle sizes were determined by means of transmission electron microscopy (TEM) if no manufacturer data was available. For further details of determination by means of TEM see Riwotzki et al., "Liquid-Phase Synthesis of Doped Nanoparticles: Colloids of Luminescing $LaPO_4$:Eu and $CePO_4$:Tb Particles with a Narrow Particle Size Distribution", J. Phys. Chem. B 2000, 104, 2824-2828.

I.e Qualitative and Quantitative Characterization of the Filler Particles

The steps described hereinafter in the qualitative and quantitative characterization of the filler particles (especially of filler particles having a particle size within a range from 25 to 120 nm) are well-known to those skilled in the art and are described in the literature.

I.e.i Resin/Filler Separation

In a first step, 1 g of a curable dental material (also referred to hereinafter as dental composite material or dental composite) is resuspended in 10 ml of acetone and the suspension obtained is then centrifuged with a centrifuge at 5000 rpm for 10 min. The supernatant (called resin phase hereinafter) is decanted off into a collection bottle and the residue is suspended in 5 ml of acetone. The mixture is centrifuged again at 5000 rpm for 10 min and decanted, and the residue is suspended again in 5 ml of acetone. The steps of centrifuging, decanting and suspending are repeated twice more under identical conditions. The total amount of residues separated from the resin phases is dried, and the total amount of resin phases is freed of acetone on a rotary evaporator.

After conducting the first step, the dried total amount of residues regularly includes those filler particles having a particle size of about 400 nm or greater than 400 nm (called macroscopic filler particles hereinafter). The total amount of resin phases freed of acetone (called resin fraction hereinafter) regularly also includes, as well as polymerizable monomers, filler particles having a particle size of about 400 nm or especially less than 400 nm (called nanoscale particles hereinafter). This method therefore ensures that the dental composite material, by virtue of the centrifugation, is separated completely into (i) a fraction of macroscopic filler particles, especially with regard to the dental glasses having a size in the order of magnitude of greater than 400 nm up to the high micrometer range, and (ii) a resin fraction including nanoscale particles.

The nanoscale particles present in the resin fraction may be both nonaggregated and nonagglomerated x-ray-opaque particles (for example filler particles of component (B1)) and non-x-ray-opaque Aerosils which, as fumed silicas, take the form of aggregates and/or agglomerates having a particle size, for example, within a range from about 150 nm to about 300 nm. Filler particles of component (B1) are regularly in the resin fraction.

The total proportion by mass of inorganic particles in the resin fraction is determined gravimetrically by difference weighing after ashing of an appropriate resin fraction.

I.e.ii TEM in Combination with EELS

In a second step, the filler particles in the resin fraction are subjected to a qualitative and quantitative characterization. For this purpose, TEM (transmission electron microscopy) is used in conjunction with EELS (electron energy loss spectroscopy).

By means of TEM, the particle sizes of the individual particles and the number thereof are determined; elemental determination of individual particles is effected by means of EELS.

To conduct the combined TEM/EELS characterization, in a first step, the concentration of the nanoscale particles in the resin fraction is first reduced by dilution with curable resin (thinner resin) (dilution: 1 part by volume of resin fraction and 99 parts by volume of thinner resin). This very substantially rules out observation of "overlapping" of nanoscale particles in the later images. Such "overlapping" would distort the particle characterization.

In a second step, bar specimens are produced by curing from the diluted resin fractions obtained by dilution with curable resin. These bar specimens are then used to produce several ultrathin sections of thickness 300 nm with an ultra-diamond knife (for example ULTRACUT UCT ultra-microtome, LEICA, Wetzlar). The ultrathin sections are transferred to copper TEM grids for stabilization. This results in thin section preparations. These thin section preparations are then analysed with acceleration voltage 120 kV in a TEM with bright field images.

A TEM analysis of the above-described thin section preparations allows distinction of nonaggregated and nonagglomerated nanoscale particles from aggregated and/or agglomerated particles (e.g. silicas, for example Aerosils) (for identification of the chemical composition see the details which follow).

If high-resolution images are to be examined, ultrathin sections having layer thicknesses of less than 100 nm can be produced and examined.

In a third step, the filler particles in the ultrathin sections or thin section preparations are chemically characterized by means of EELS point analyses, such that the chemical composition of individual particles becomes known (for determination of the surface modification of particles see point I.f below).

The volume- or weight-based proportions of particle fractions (including a plurality thereof if appropriate) are determined in a fourth step from a TEM image as follows: the image section from a TEM image viewed under a microscope is an area having edge lengths a and b which are determined by means of the legend. Multiplying by the thickness c of the ultrathin section gives a total volume $V_{total}$ for the area under consideration in the TEM. This total volume $V_{total}$ is the sum total of the resin volume $V_{resin}$ and the volume of all the particles $V_{particles}$ within this volume (the volume of all the particles may include several groups of particles, for example sorted by various criteria, for example size). The following equation holds: $V_{total}=a*b*c=V_{resin}+V_{particles}$.

The volume of individual particles (and hence the volume of all the particles in the volume under consideration) is obtainable by calculation via the sphere volume of the individual particles. For this purpose, in the TEM image, the diameter or radius of an appropriate particle is determined. The sphere volume calculated therefrom, multiplied by the density of the corresponding material of which the particle consists (material identifiable by means of EELS), gives the mass of the particle. The resin volume, obtainable from the total volume minus the particle volume, multiplied by the resin density, gives the resin mass. The resin density results from the density of the resin used for dilution and, if appropriate, the density of the diluted resin fraction (the latter can possibly be neglected in the calculation of the resin density if the proportion of the diluted resin is negligible). The proportion of the particles (or a group of particles) in percent by weight is calculated from $m_p*100/(m_{particles}+m_{resin})$ where $m_p$ is the mass of the particle fraction under consideration in the volume under consideration, $m_{particles}$ is the mass of all the particles in the volume under consideration and $m_{resin}$ is the mass of the resin in the volume under consideration. In the final calculation of the proportion by weight of the particle fraction under consideration, the dilution factor is taken into account appropriately.

I.f Determination of Organic Surface Modifications

I.f.i Preliminary Assessment

Many known x-ray-opaque filler materials (for example ytterbium fluoride or barium sulphate) have the disadvantage that they can be incorporated only with difficulty into the matrix (resin matrix) composed of polymerizable monomers (called the organic resin phase) because they do not enter into sufficient chemical bonds (binding opportunities) with the hydrophobic groups of the medium. Vitreous fillers can be incorporated in an excellent manner into the resin matrix of dental composite materials, for example, with the aid of silanization via Si—OH groups. In the case of ytterbium fluoride and barium sulphate, no such groups are present on the surfaces; they are therefore not silanizable and lead to inadequate physical and chemical resistance in a cured dental material (see WO 2005/011621 A1, bottom of page 2).

The x-ray-opaque nanoscale particles used in a curable dental material of the invention therefore will not have any silanes on their surfaces. Instead, the linking is effected via nitrogen, oxygen, sulphur and/or phosphorus atoms (again, see WO 2005/011621 A1 and our remarks further up in the text).

I.f.ii Removal of Polymerizable Monomers from Nanoscale Particles

I.f.ii.a "Cross-Flow" Method

The removal of polymerizable monomers from nanoscale particles is effected, for example, in a "cross-flow" method known to those skilled in the art by means of ultrafiltration membranes.

In this method, a resin fraction (as already described above) comprising nanoscale particles, polymerizable monomers and optionally a suitable diluent is pumped from a vessel by means of a pump into a circuit composed of particular membranes, and the polymerizable monomers pass through the pores of the membranes and are separated as filtrate, while the nanoscale particles remain within the circuit (and hence within the vessel).

An example of a suitable system for this separating step is the "Vivaflow 50" system from "Sartorius Stedim Biotech GmbH, Göttingen". The pump drive (7554-95) and pump head come from the "Masterflex L/S" series from "Cole Parmer Instrument Co.", Illinois, USA. The operation of the pump is set to 2.5 bar during the filtration. Two separation membranes of the "50,000 MWCO (PES)" type are connected in series. The MWCO (molecular weight cutoff) defines the separation limit here, i.e. the size of the molecules which can still pass efficiently through the membrane. This value is reported in daltons. The fractions obtained are subsequently analysed as described in point I.f.iii.

I.f.ii.b Sedimentation Field-Flow Fractionation (SF3)

As an alternative to a procedure as described in step I.f.ii.a, it is possible to conduct a sedimentation field-flow fractionation (SF3). This can especially separate different particle fractions from one another and additionally from the resin fraction. It is a prerequisite here that the different particle fractions differ sufficiently from one another in terms of size and/or density.

Corresponding equipment containing a separation column necessary for the purpose is obtainable from Postnova Analytics GmbH, Landsberg. The module containing the separation column is identified as CF2000 Centrifugal FFF and is supplemented by the further modules PN7140 (Eluent Organizer), PN1130 (Isocratic Pump), PN5300 (Autosampler), PN3621 MALS (21-Multi-Angle Light Scattering Detector) and PN8050 (Fraction Collector). In this combination, the Centrifugal FFF system allows not just the analytical but also the preparative separation of particle fractions. The fractions obtained are subsequently analysed as described in point I.f.iii.

I.f.iii Characterization of the Surface Modification

A sample which has been produced according to I.f.ii.a and then freed of solvents, containing nanoscale particles in the form of a powder, or a sample produced according to I.f.ii.b, is subsequently examined by means of spectroscopic methods (for example by means of $^1$H NMR, $^{13}$C NMR, $^{15}$N NMR, $^{29}$Si NMR and $^{31}$P NMR, and also IR).

Signals which cannot be attributed to a silane, for example the gamma-methacryloyloxypropylsilyl radical, are attributed to organic surface modifications not based on silanes, for example surface modifications by means of organic compounds on surfaces of ytterbium fluoride or barium sulphate particles.

The proportions of organically surface-modified particles and/or non-organically surface-modified particles can also be determined regularly by evaluation of the intensities of corresponding vibration bands in the IR spectrum. For this purpose, reference vibration bands (reference curves) of organically surface-modified or non-organically surface-modified particles with the corresponding chemical compositions are conventionally employed.

I.g Alternative Characterization by Means of Image Analysis and Raman Spectroscopy The person skilled in the art is aware of additional methods and coupled methods which allow qualitative and quantitative characterization of the filler particles. In this respect, reference is made, for example, to the article "Chemische Identität einzelner Partikel" [Chemical Identity of Individual Particles] by Deborah Huck-Jones and Renate Hessemann in "Nachrichten aus der Chemie", Volume 62, September 2014, pages 886 and 887. The combination of image analysis and Raman spectroscopy disclosed therein is regularly also suitable for characterization of the filler particles in the context of the present invention. This is especially true of samples which are obtained by the resin/filler separation described above. An example of a suitable image analysis is again the TEM analysis described in the text above.

II. Curable Dental Materials

II.a Composition of Inventive and Non-Inventive Curable Dental Materials

All the figures given in Table 1 are percentages by weight. The identifier "Ref" relates to non-inventive compositions of curable dental materials.

TABLE 1

| | Starting material | A (Ref) | B | C | D | E (Ref) | F | G | H |
|---|---|---|---|---|---|---|---|---|---|
| (A) | UDMA | 10.74 | 10.74 | 10.74 | 10.74 | 10.74 | 10.74 | 10.74 | 10.74 |
| | TCD-DMA | 10.74 | 10.74 | 10.74 | 10.74 | 10.74 | 10.74 | 10.74 | 10.74 |
| (C) | TinuvinP | 0.09 | 0.09 | 0.09 | 0.09 | 0.09 | 0.09 | 0.09 | 0.09 |
| | MeHQ | 0.02 | 0.02 | 0.02 | 0.02 | 0.02 | 0.02 | 0.02 | 0.02 |
| | CQ | 0.06 | 0.06 | 0.06 | 0.06 | 0.06 | 0.06 | 0.06 | 0.06 |
| | DABE | 0.10 | 0.10 | 0.10 | 0.10 | 0.10 | 0.10 | 0.10 | 0.10 |
| (B) | Dental glass 1 (1.5 µm) | 50.00 | 50.00 | 50.00 | 50.00 | — | — | — | — |
| | Dental glass 1 (0.7 µm) | 16.66 | 16.66 | 16.66 | 16.66 | — | — | — | — |
| | Dental glass 2 (1.5 µm) | — | — | — | — | 50.00 | 50.00 | 50.00 | 50.00 |
| | Dental glass 2 (0.7 µm) | — | — | — | — | 16.66 | 16.66 | 16.66 | 16.66 |
| | Ytterbium fluoride | 11.59 | 11.59 | 11.59 | 11.59 | 0 | 0 | 0 | 0 |
| | Barium sulphate | 0 | 0 | 0 | 0 | 11.59 | 11.59 | 11.59 | 11.59 |

As described above, the abbreviation "UDMA" relates to the chemical compound 7,7,9-trimethyl-4,13-dioxo-5,12-diazahexadecane 1,16-dioxydimethacrylate.

The abbreviation "TCD-DMA" relates to the chemical compound bis(methacryloyloxymethyl)tricyclo[5.2.1.0$^{2,6}$]decane.

As described above, the abbreviation "MeHQ" relates to the chemical compound hydroquinone monomethyl ether.

The abbreviation "CQ" relates to the chemical compound camphor quinone.

The abbreviation "DABE" relates to the chemical compound ethyl-p-N,N-dimethylaminobenzoate.

The curable dental materials A to H differ as follows:

The curable dental materials A to D comprise nonaggregated, nonagglomerated, organically surface-modified filler particles of ytterbium fluoride. These filler particles differ in terms of their particle sizes as follows (the figures for D10, D50 and D90 are volume-based particle sizes in nm):

non-inventive curable dental material A: particle size distribution: D10: 12 nm, D50: 15 nm, D90: 20 nm inventive curable dental material B: particle size distribution: D10: 26 nm, D50: 30 nm, D90: 39 nm inventive curable dental material C: particle size distribution: D10: 38 nm, D50: 50 nm, D90: 65 nm together with the resin mixture, and the resulting mixture was homogenized by stirring and freed of the solvent on a rotary evaporator. Subsequently, the refractive index "resin and YbF$_3$" or "resin and BaSO$_4$" was determined (cf. Table 2 below).

In a third step, the auxiliaries (C) were introduced into the homogenized mixture which had been freed of solvent and resulted from step 2 while stirring.

In a fourth step, component (B2) of the particulate fillers (the dental glasses) was incorporated into the mixture (of components (A), (B1) and (C)) that resulted from the third step by means of the Hauschild AM 501 mixing system and then processed to give a homogeneous pasty mass (4*12 s) which was freed of air at 50 rpm and −0.85 bar in a laboratory kneader with blade stirrers (PC Laborsystem, Magden, CH) for 10 min.

II.c Refractive Indices of Selected Components of the Curable Dental Materials A to H

TABLE 2

| | A (Ref) | B | C | D | E (Ref) | F | G | H |
|---|---|---|---|---|---|---|---|---|
| Refractive index: $n_A$ (resin) | 1.4941 | 1.4941 | 1.4941 | 1.4941 | 1.4941 | 1.4941 | 1.4941 | 1.4941 |
| Refractive index: resin and YbF$_3$ | 1.5153 | 1.5153 | 1.5153 | 1.5153 | — | — | — | — |
| Refractive index: resin and BaSO$_4$ | — | — | — | — | 1.5448 | 1.5448 | 1.5448 | 1.5448 |
| Refractive index: $n_{B2}$ (glasses) | 1.5300 | 1.5300 | 1.5300 | 1.5300 | 1.5500 | 1.5500 | 1.5500 | 1.5500 | inventive curable dental material D: particle size distribution: D10: 69 nm, D50: 90 nm, D90: 117 nm The curable dental materials E to H comprise nonaggregated, nonagglomerated, organically surface-modified filler particles of barium sulphate. These filler particles differ in terms of their particle sizes as follows:

non-inventive curable dental material E: particle size distribution: D10: 11 nm, D50: 15 nm, D90: 20 nm inventive curable dental material F: particle size distribution: D10: 25 nm, D50: 30 nm, D90: 40 nm inventive curable dental material G: particle size distribution: D10: 38 nm, D50: 50 nm, D90: 67 nm inventive curable dental material H: particle size distribution: D10: 68 nm, D50: 90 nm, D90: 120 nm TinuvinP is a UV stabilizer, MeHQ an inhibitor, CQ an initiator and DABE a coinitiator. The filler content of each of the curable dental materials A to H is 78.26%.

II.b Production of the Curable Dental Materials A to H

In a first step, for the production of the individual curable dental materials A to H, the polymerizable monomers of the total amount (A) were dissolved in one another while stirring. The result was a resin mixture, and the refractive index "$n_A$ (resin)" thereof was subsequently determined (cf. Table 2 below).

In a second step, component (B1) of the particulate fillers (ytterbium fluoride or barium sulphate in the form of a colloidal solution in ethanol) was weighed into a flask The refractive indices "resin and YbF$_3$" and "resin and BaSO$_4$" are based on the uncured state. Comparative studies have shown that addition of appropriate catalysts and curing of such mixtures causes the refractive index of these cured mixtures to move even closer to the refractive indices of the dental glasses.

III. Cured Dental Materials

III.a Production of the Cured Dental Materials A to H

The cured dental materials A to H are the cured curable dental materials A to H.

The curable dental materials A to H produced according to point II.b were converted to the cured dental materials A to H by irradiation with blue light of wavelength 470 nm with the Celalux II LED polymerization lamp from VOCO.

The test specimens for determination of translucence (diameter 15 mm, height 2 mm) and x-ray opacity (diameter 15 mm, height 1 mm) were produced using Teflon moulds, into which the curable dental materials were introduced, and they were covered with PET film to prevent an inhibition layer and pressed between two glass plates. The light exit window of the polymerization lamp was placed onto the upper glass plate and a region of the material was irradiated for 10 s. Subsequently, the light exit window was moved onward and a further region that overlapped with the first was irradiated. This procedure was continued until the particular test specimen had been fully cured by irradiation.

III.b Properties of the Cured Dental Materials A to H Produced

TABLE 3

|  | A (Ref) | B | C | D | E (Ref) | F | G | H |
|---|---|---|---|---|---|---|---|---|
| Translucence [%] | 58.7 | 63.2 | 66.8 | 47.4 | 61.3 | 67.5 | 64.4 | 59.6 |
| X-ray opacity [mm Al] | 4.1 | 4.1 | 4.1 | 4.1 | 3.9 | 3.9 | 3.9 | 3.9 |

IV. DVT Measurements

IV.a Production of Test Specimens A to H for DVT Measurements

The test specimens A to H correspond to cured dental materials A to H (see point III.a. above).

Test specimens A to H were produced from the corresponding curable dental materials (cf. Table 1 above and point II.b above). In a first step, the appropriate curable dental material was introduced into a 2 mm×2 mm×2 mm Teflon mould. The curable dental material was cured according to the above point III.a. After removal from the moulds, the result was cured dental materials (each a corresponding test specimen) each having the dimensions 2 mm×2 mm×2 mm.

In a next step, each test specimen was fixed in epoxy resin (embedding compound). This was done by fixing each test specimen on one side in the epoxy resin.

IV.b Procedure for the DVT Measurements

The DVT measurements were conducted with the CS 9300 DVT instrument from Carestream Health Inc. in the Teeth_5×5_HR_IB recording mode. The size of the 567× 567×561 voxels in this mode was 90 μM. The tube voltage was 65 kV at a tube current of 2 mA.

IV.c Evaluation of the DVT Images Obtained by Means of DVT Measurements

The evaluation of the DVT images is based on 11 to 12 two-dimensional cross sections (individual tomograms) which were obtained from a DVT measurement for each test specimen. These 11 to 12 two-dimensional cross sections (individual tomograms) were evaluated with respect to the artefacts specified hereinafter. FIG. 1 shows, by way of example, the artefacts specified hereinafter in a two-dimensional cross section of an example test specimen (in FIG. 1: x).

A: black stripes which start from the corners of the test specimen and run vertically upward and downward in the two-dimensional cross sections B: white stripes which start from at least one corner of the test specimen and run diagonally in the two-dimensional cross sections C: the test specimens do not appear to be rectangular in the two-dimensional cross sections, but to have edges curving outward D: white stripes to the right and/or left of the test specimens (similar to a comet's tail)

In FIG. 1, y means the resin used for fixing of the test specimen x (fixing resin).

The evaluation of the two-dimensional cross sections involved checking, in each cross section, (i) whether it was possible to identify one of the abovementioned artefacts and (ii) the intensity with which it occurred. We have summarized the evaluation of the two-dimensional cross sections for the test specimens of the cured dental materials A to H in tables hereinafter. The symbols in the tables which follow have the following meanings:

- not visible
o barely perceptible
+ visible
++ clearly visible
n.a. no data measured The table heading of each of the tables which follow indicates which cured dental material was examined. The first column (on the left) gives the abovementioned artefacts. The identifier "A.01" (cf., for example, Table 4) means that this is the first of the 11 or 12 two-dimensional cross sections. The same applies to Tables 5 to 11.

TABLE 4

| | A (Ref) (non-inventive) | | | | | | | | | | | |
|---|---|---|---|---|---|---|---|---|---|---|---|---|
| | A.01 | A.02 | A.03 | A.04 | A.05 | A.06 | A.07 | A.08 | A.09 | A.10 | A.11 | A.12 |
| A | o | ++ | + | ++ | ++ | + | ++ | ++ | + | ++ | + | ++ |
| B | ++ | o | + | ++ | o | o | + | − | − | − | o | − |
| C | ++ | ++ | ++ | ++ | ++ | ++ | ++ | ++ | ++ | ++ | ++ | ++ |
| D | o | + | + | o | + | + | o | + | + | o | + | ++ |

TABLE 5

| | B (inventive) | | | | | | | | | | | |
|---|---|---|---|---|---|---|---|---|---|---|---|---|
| | B.01 | B.02 | B.03 | B.04 | B.05 | B.06 | B.07 | B.08 | B.09 | B.10 | B.11 | B.12 |
| A | o | o | + | o | o | − | + | o | − | o | o | o |
| B | − | + | + | o | o | o | o | + | o | o | o | o |
| C | + | + | + | + | + | + | + | + | + | + | + | + |
| D | − | o | − | − | − | − | − | − | o | o | − | + |

TABLE 6

| | \multicolumn{12}{c}{C (inventive)} |
|---|---|---|---|---|---|---|---|---|---|---|---|---|
| | C.01 | C.02 | C.03 | C.04 | C.05 | C.06 | C.07 | C.08 | C.09 | C.10 | C.11 | n.a. |
| A | − | o | o | o | − | o | o | − | o | o | − | n.a. |
| B | − | o | o | o | o | o | o | o | o | + | o | n.a. |
| C | + | + | + | + | + | + | + | + | + | + | + | n.a. |
| D | − | o | o | − | − | o | − | − | − | − | o | n.a. |

TABLE 7

| | \multicolumn{12}{c}{D (inventive)} |
|---|---|---|---|---|---|---|---|---|---|---|---|---|
| | D.01 | D.02 | D.03 | D.04 | D.05 | D.06 | D.07 | D.08 | D.09 | D.10 | D.11 | D.12 |
| A | − | o | o | o | o | o | o | o | − | o | o | − |
| B | + | o | o | + | o | o | + | + | − | − | o | o |
| C | + | + | + | + | + | + | + | + | + | + | + | + |
| D | − | − | o | − | − | o | − | o | o | o | o | o |

TABLE 8

| | \multicolumn{12}{c}{E (Ref) (non-inventive)} |
|---|---|---|---|---|---|---|---|---|---|---|---|---|
| | E.01 | E.02 | E.03 | E.04 | E.05 | E.06 | E.07 | E.08 | E.09 | E.10 | E.11 | E.12 |
| A | + | + | o | + | + | + | + | + | + | ++ | + | o |
| B | o | + | + | o | o | o | o | o | o | + | + | o |
| C | + | ++ | ++ | ++ | ++ | ++ | ++ | + | ++ | ++ | ++ | + |
| D | − | − | o | − | o | o | − | o | + | o | o | + |

TABLE 9

| | \multicolumn{12}{c}{F (inventive)} |
|---|---|---|---|---|---|---|---|---|---|---|---|---|
| | F.01 | F.02 | F.03 | F.04 | F.05 | F.06 | F.07 | F.08 | F.09 | F.10 | F.11 | F.12 |
| A | − | o | − | o | o | o | + | o | − | o | − | − |
| B | + | + | o | o | + | o | o | + | o | o | o | o |
| C | + | + | + | + | + | ++ | + | + | + | + | + | + |
| D | − | − | o | − | o | o | o | o | + | − | − | o |

TABLE 10

| | \multicolumn{12}{c}{G (inventive)} |
|---|---|---|---|---|---|---|---|---|---|---|---|---|
| | G.01 | G.02 | G.03 | G.04 | G.05 | G.06 | G.07 | G.08 | G.09 | G.10 | G.11 | G.12 |
| A | o | o | o | o | − | − | − | o | − | o | − | − |
| B | + | + | + | o | + | o | + | o | o | + | − | − |
| C | + | + | + | + | + | + | + | + | + | + | + | + |
| D | − | o | − | − | o | o | − | o | o | − | o | o |

TABLE 11

| | \multicolumn{12}{c}{H (inventive)} |
|---|---|---|---|---|---|---|---|---|---|---|---|---|
| | H.01 | H.02 | H.03 | H.04 | H.05 | H.06 | H.07 | H.08 | H.09 | H.10 | H.11 | H.12 |
| A | o | − | − | o | o | o | + | + | − | − | o | o |
| B | + | + | o | o | o | o | o | o | − | − | o | o |
| C | ++ | + | + | + | + | ++ | ++ | + | + | + | + | + |
| D | o | o | o | − | − | o | o | o | o | − | o | o |

The two-dimensional cross sections of the respective DVT images of the cured dental materials A and E (non-inventive) show comparatively more and especially more marked artefacts as compared with the two-dimensional cross sections of the respective DVT images of the cured dental materials B, C, D and F to H (inventive), in DVT measurements conducted in an otherwise identical manner (cf. point IV.b above).

V. Free-Flowing Inventive Curable Dental Material 50 g of the inventive curable dental material C (cf. Table 1 above in the text) were additionally combined with 5 g of TEGDMA (triethylene glycol dimethacrylate) and 1.5 g of Aerosil R711 (Evonik), then rolled in an Exakt 80 E three-roll mill (Exakt GmbH, Norderstedt) and subsequently freed of air at 50 rpm and −0.85 bar in a laboratory kneader having blade stirrers (PC Laborsystem, Magden, CH) for 10 min. The result was an inventive curable dental material that was free-flowing under shear ("flow composite") (curable dental material J). This free-flowing inventive dental material J was used to produce test specimens in an analogous manner to Examples A-H. For these test specimens, a translucence of 54.3% was determined, and an x-ray opacity of 3.6 mm Al. In the DVT, predominantly images having a low level of artefacts were obtained.

The invention claimed is:

1. A curable dental material produced by mixing starting materials, wherein the starting materials to be mixed are exclusively:
   one or more polymerizable monomers which form the total amount (A) of the polymerizable monomers in the curable dental material,
   one or more particulate fillers which form the total amount (B) of the particulate fillers in the curable dental material, and
   one or more auxiliaries which form the total amount (C) of the auxiliaries in the curable dental material,
wherein the total amount (A) of the polymerizable monomers has a refractive index $n_A$ in the range from 1.45 to 1.55,
wherein the curable dental material comprises a component (B1) which forms part of the total amount (B), comprising:
   (a) nonaggregated and nonagglomerated filler particles having a particle size in the range from 25 to 120 nm of ytterbium fluoride or
   (b) nonaggregated and nonagglomerated filler particles having a particle size in the range from 25 to 120 nm of barium sulphate, or
   (c) both (a) and (b),
wherein the proportion of component (B1) is
   at least 2.5% by weight based on the total mass of the curable dental material, and
   at least 90% based on the total mass of filler particles of ytterbium fluoride and barium sulphate in the curable dental material.

2. The curable dental material according to claim 1, wherein the total amount (A) of the polymerizable monomer(s) has a refractive index $n_A$ in the range from 1.48 to 1.55.

3. The curable dental material according to claim 1, wherein the proportion of component (B1) is within a range from 2.5% by weight to 20% by weight based on the total mass of the curable dental material.

4. The curable dental material according to claim 1, wherein the total amount (B) of the particulate fillers consists of component (B1) and a component (B2), wherein the total amount of the particulate fillers in component (B2) has a refractive index $n_{B2}$ in the range from 1.49 to 1.62.

5. The curable dental material according to claim 1, wherein the proportion of the total amount (B) is in the range from 72% to 92% by weight based on the total amount of the starting materials to be mixed.

6. The curable dental material according to claim 1, wherein:
   the curable dental material has an x-ray opacity of 3.5 mm Al or greater and/or
   by polymerizing polymerizable monomers in the curable dental material it is possible to obtain a cured dental material having an x-ray opacity of 3.5 mm Al or greater.

7. The curable dental material according to claim 1, wherein 70% by weight or more of the particulate fillers which form the total amount (B) of the particulate fillers in the curable dental material have been organically surface-modified.

8. The curable dental material according to claim 1, wherein component (B1) comprises:
   (a) nonaggregated and nonagglomerated filler particles having a particle size in the range from 30 to 100 nm of ytterbium fluoride or
   (b) nonaggregated and nonagglomerated filler particles having a particle size in the range from 30 to 100 nm of barium sulphate or
   (c) both (a) and (b).

9. The curable dental material according to claim 1, wherein the starting materials to be mixed are exclusively:
   in a total amount in the range from 7.95% to 27.95% by weight, based on the total mass of the starting materials to be mixed, one, two, three or more than three polymerizable monomers which form the total amount (A) of the polymerizable monomers in the curable dental material, wherein the total amount (A) of the polymerizable monomer(s) has a refractive index $n_A$ within a range from 1.45 to 1.55,
   in a total amount in the range from 72% to 92% by weight, based on the total mass of the starting materials to be mixed, one, two, three or more than three particulate fillers which form the total amount (B) of the particulate fillers in the curable dental material,
   in a total amount in the range from 0.05% to 2% by weight, based on the total mass of the starting materials to be mixed, one, two, three or more than three auxiliaries which form the total amount (C) of the auxiliaries in the curable dental material,
wherein the curable dental material comprises a component (B1) which forms part of the total amount (B), comprising of the total amount of the following that are present in the curable dental material:
   (a) nonaggregated and nonagglomerated filler particles having a particle size in the range from 25 to 120 nm of ytterbium fluoride, and
   (b) nonaggregated and nonagglomerated filler particles having a particle size in the range from 25 to 120 nm of barium sulphate,
wherein the proportion of component (B1) is
   2.5% by weight or greater based on the total mass of the curable dental material and
   90% by weight or greater based on the total mass of filler particles of ytterbium fluoride and barium sulphate in the curable dental material and
   the total amount of the particulate fillers in component (B1) has a refractive index $n_{B1}$ in the range from 1.55 to 1.64.

10. A cured dental material obtained by polymerizing polymerizable monomers in a curable dental material according to claim 1.

11. A method of producing a dental product, comprising:
   producing or providing a curable dental material according to claim 1, and
   curing the curable dental material into a dental product;
   wherein the producing is not effected in a human or animal body,
   wherein the dental product is selected from the group consisting of artificial teeth, inlays, onlays, crowns, bridges, mill blanks, implants and dentures.

12. A method for producing a curable dental material according to claim 1, comprising:
  (i) producing or providing a plurality of starting materials, or producing or providing partial mixtures of the plurality of starting materials,
  (ii) mixing the starting materials produced or provided in (i) or the partial mixtures produced or provided in (i), so as to result in the curable dental material in each case,
  wherein the plurality of starting materials comprise
    one or more polymerizable monomers which form the total amount (A) of the polymerizable monomers in the curable dental material,
    one or more particulate fillers which form the total amount (B) of the particulate fillers in the curable dental material, and
    one or more auxiliaries which form the total amount (C) of the auxiliaries in the curable dental material,
  wherein the curable dental material comprises a component (B1) which forms part of the total amount (B), comprising:
    (a) nonaggregated and nonagglomerated filler particles having a particle size in the range from 25 to 120 nm of ytterbium fluoride, or
    (b) nonaggregated and nonagglomerated filler particles having a particle size in the range from 25 to 120 nm of barium sulphate, or
    (c) both (a) and (b),
  wherein the proportion of component (B1) is
    2.5% by weight or greater than 2.5% by weight, based on the total mass of the curable dental material, and
    90% by weight or greater than 90% by weight, based on the total mass of filler particles of ytterbium fluoride and barium sulphate in the curable dental material.

13. A method for producing a cured dental material according to claim 10, comprising:
  (I) producing or providing a curable dental material, and
  (II) polymerizing polymerizable monomers in the curable dental material, so as to result in the cured dental material,
  wherein the curable dental material comprises:
    one or more polymerizable monomers which form the total amount (A) of the polymerizable monomers in the curable dental material,
    one more particulate fillers which form the total amount (B) of the particulate fillers in the curable dental material, and
    one or more auxiliaries which form the total amount (C) of the auxiliaries in the curable dental material,
  wherein the curable dental material comprises a component (B1) which forms part of the total amount (B), comprising:
    (a) nonaggregated and nonagglomerated filler particles having a particle size in the range from 25 to 120 nm of ytterbium fluoride, or
    (b) nonaggregated and nonagglomerated filler particles having a particle size in the range from 25 to 120 nm of barium sulphate, or
    (c) both (a) and (b),
  wherein the proportion of component (B1) is
    2.5% by weight or greater than 2.5% by weight, based on the total mass of the curable dental material, and
    90% by weight or greater than 90% by weight, based on the total mass of filler particles of ytterbium fluoride and barium sulphate in the curable dental material.

14. A kit comprising:
  one or more than one dental syringe and
  (i) one or more curable dental materials according to claim 1, and/or
  (ii) one or more base pastes and one, two or more than two catalyst pastes, wherein the curable dental material according to claim 1 is obtained by mixing a base paste and the corresponding catalyst paste.

15. A method for a diagnostic method or dental treatment of a patient, comprising:
  (1) producing or providing a curable dental material according to claim 1,
  (2) introducing and positioning the curable dental material produced or provided in the patient's oral cavity and curing the curable dental material or introducing and positioning the cured dental material produced or provided in the patient's oral cavity.

16. The method of claim 15, wherein the method comprises using the curable dental material for a treatment selected from the group consisting of:
  temporary or permanent filling of a dental cavity,
  tooth filling material,
  dental cement,
  dental lining material,
  a free-flowing composite material (flow material),
  a crown material,
  an inlay and/or onlay,
  a bridge material and/or
  a core build-up material.

17. The method for producing a cured dental material according to claim 13, wherein:
  (a) nonaggregated and nonagglomerated filler particles having a particle size in the range from 25 to 120 nm of ytterbium fluoride and
  (b) nonaggregated and nonagglomerated filler particles having a particle size in the range from 25 to 120 nm of barium sulphate, are included in the curable dental material as x-ray-opaque filler in a curable dental material.

18. A method for producing a dental product by means of an additive manufacturing method that uses a digital data model, comprising the steps of:
  producing or providing a curable dental material according to claim 1,
  processing the curable dental material produced or provided in an additive manufacturing method that uses a digital data model, so as to result in the dental product or a precursor of the dental product,
  wherein the dental product is selected from the group comprising of artificial teeth, inlays, onlays, crowns, bridges, mill blanks, implants and dentures.

19. The curable dental material according to claim 1, wherein the filler particles of component (B1) have been organically surface-modified by a first functional group selected from the group consisting of a phosphate, a phosphonate, a carboxylate, a dithiophosphate, a dithiophosphonate, an amine and an amide linked to a second functional group selected from the group consisting of linear or branched alkyl, arenyl and alkenyl groups.

20. The curable dental material according to claim 19, wherein the first functional group and the second functional group are linked together by a linker selected from the group consisting of linear or branched alkyl chains, aromatic groups, and combinations thereof, each of which may be interrupted by heteroatoms selected from the group consisting of O, N, S, and P.

* * * * *